(12) United States Patent
Kim

(10) Patent No.: US 8,178,013 B2
(45) Date of Patent: May 15, 2012

(54) PLGA/HYDROXYAPATITE COMPOSITE BIOMATERIAL BY GAS BUBBLE FORMATION

(75) Inventor: Byung-Soo Kim, Irvine, CA (US)

(73) Assignee: Nano Orthopedics, LLC, Boca Raton, FL (US)

( * ) Notice: Subject to any disclaimer, the term of this patent is extended or adjusted under 35 U.S.C. 154(b) by 436 days.

(21) Appl. No.: 11/714,507

(22) Filed: May 22, 2007

(65) Prior Publication Data

US 2008/0065228 A1 Mar. 13, 2008

Related U.S. Application Data

(60) Provisional application No. 60/767,137, filed on Mar. 6, 2006.

(51) Int. Cl.
| | |
|---|---|
| *B29C 45/76* | (2006.01) |
| *B29C 45/17* | (2006.01) |
| *B29C 59/00* | (2006.01) |
| *D04H 1/00* | (2006.01) |
| *C04B 40/00* | (2006.01) |
| *B27N 3/00* | (2006.01) |

(52) U.S. Cl. ........ 264/40.5; 264/40.3; 264/122; 264/82; 264/109

(58) Field of Classification Search .................. None
See application file for complete search history.

(56) References Cited

U.S. PATENT DOCUMENTS

| 5,626,861 | A | 5/1997 | Laurencin et al. |
| 6,165,486 | A | 12/2000 | Marra et al. |
| 6,517,583 | B1 | 2/2003 | Pope et al. |
| 2005/0031694 | A1 | 2/2005 | Gilbertson et al. |
| 2008/0065228 | A1* | 3/2008 | Kim ........................... 623/23.61 |

OTHER PUBLICATIONS

Kim, et al. (2006) Biomaterials, 27: 1399-409.*
De Boer, H. H., The History of Bone Grafts, Clinical Orthopedics and Related Research, 1998, pp. 292-298, 226.
Bonfiglio, M. et al., Immunological Responses to Bone, Clinical Orthopedics and Related Research, 1972, pp. 19-27, 87.
Coombes, A. G. A. et al., Resorbable Synthetic Polymers as Replacements for Bone Graft, Clinical Materials, 1994, pp. 35-67, 17.
Rizzi, S. C. et al., Biodegradable Polymer/hydroxyapatite Composites: Surface Analysis and Initial Attachment of Human Osteoblasts, J Biomed Mater Res, 2001, pp. 475-86, 55.
Laurencin, C. T. et al., Advancements in Tissue Engineered Bone Substitutes, Current Opinion in Orthopedics, 1999, pp. 445-451, 10.
Ambrosio, A. M. A. et al., A Novel Amorphous Calcium Phosphate Polymer Ceramic for Bone Repair: I. Synthesis and Characterization, J Biomed Mater Res, 2001, pp. 295-301, 58.
Marra, K. G. et al., In vitro Analysis of Biodegradable Polymer Blend/hydroxyapatite Composites for Bone Tissue Engineering, J Biomed Mater Res., 1999, pp. 324-335, 47.
Wang, M., Developing Bioactive Composite Materials for Tissue Replacement, Biomaterials, 2003, pp. 2133-2151, 24.
Van Landuyt, P. et al., The Influence of High Sintering Temperatures on the Mechanical Properties of Hydroxyapatite, J Mater Sci: Mater Med, 1995, pp. 8-13, 6. (Abstract Only).
Khan, Y. M. et al., Novel Polymer-Synthesized Ceramic Composite-Based System for Bone Repair: An in vitro Evaluation, J Biomed Mater Res, 2004, pp. 728-737, 69.
Piattelli, A. et al., Resorption of Composite Polymer-Hydroxyapatite Membranes: A Time-Course Study in Rabbit, Biomaterials, 1996, pp. 629-633, 18.
Lu, L. et al., Synthetic Bone Substitutes, Current Opinion in Orthopedics, 2000, pp. 383-390, 11.
Peter, S. J. et al., Marrow Stromal Osteoblast Function on a Poly(propylene fumarate)/ beta-tricalcium Phosphate Biodegradable Orthopaedic Composite, Biomaterials, 2000, pp. 1207-1213, 21.
Wei, G. et al., Structure and Properties of Nano-hydroxyapatite/polymer Composite Scaffolds for Bone Tissue Engineering, Biomaterials, 2004, pp. 4749-4757, 25.
Guan, L. et al., Preparation and Characterization of a Highly Macroporous Biodegradable Composite Tissue Engineering Scaffold, J Biomed Mater Res, 2004, pp. 480-487, 71.
Zhang, R. et al., Poly(alpha-hydroxyl acids)/hydroxyapatite Porous Composites for Bone-Tissue Engineering. I. Preparation and Morphology, J Biomed Mater Res, 1999, pp. 446-455, 44.
Lee, S. et al., Thermally Produced Biodegradable Scaffolds for Cartilage Tissue Engineering, Macromolecular Bioscience, 2004, pp. 802-810, 4.

(Continued)

*Primary Examiner* — Robert M Kelly
(74) *Attorney, Agent, or Firm* — Roetzel & Andress; Michael J. Keller

(57) ABSTRACT

Tissue engineering is a growing field where new materials are being developed for implantation into the body. One important area involves bone graft materials to replace areas of bone lost to trauma or disease. Traditionally, graft material may be harvested from the bone of the individual receiving the graft material. However, this requires an additional surgery and additional recovery. Bone also may be taken from others, or even cadavers, but this introduces biocompatibility problems as well as the risk of disease transfer. Ideally, a biocompatible material is sought that will act as a filler with appropriate mechanical strength, encourage bone healing, and degrade to allow new bone ingrowth without the risk of disease transfer. The present invention is a new composite bone graft material made from biocompatible poly(D,L-lactic-co-glycolic acid) (PLGA) and nano-sized hydroxyapatite particles exposed on its surface using a gas foaming particle leaching (GF/PL) method. A further embodiment of this invention involves coating this PLGA/hydroxyapatite biomaterial with an adherent, fast, uniform coating of a mineral such as apatite. The PLGA polymer portion of the composite provides sufficient mechanical strength to replace bone and is degradable over time to allow new bone tissue ingrowth. The incorporated hydroxyapatite particles increase the composite material's osteogenic properties by providing sites for tissue attachment and propagation. Finally, a uniform coating of mineral apatite on the surface of this novel biomaterial composite further enhances its osteogenic qualities.

10 Claims, 31 Drawing Sheets

OTHER PUBLICATIONS

Yang, S. et al., The Design of Scaffolds for Use in Tissue Engineering. Part I. Traditional Factors, Tissue Engineering, 2001, pp. 679-689, 7.

Jung, Y. et al., A poly(lactic acid)/calcium Metaphosphate Composite for Bone Tissue Engineering, Biomaterials, 2005, pp. 6314-6322, 26.

Jung, Y. et al., Tissue Engineered Bone Formation with Polymer/ceramic Composites by Press-and-Baking Method, Key Engineering Materials, 2005, pp. 79-82, 288.

Harris, L. D. et al., Open Pore Biodegradable Matrices Formed With Gas Foaming, J Biomed Mater Res, 1998, pp. 396-402, 42.

Cho, S. et al., Smooth Muscle-Like Tissues Engineered With Bone Marrow Stromal Cells, Biomaterials, 2004, pp. 2979-2986, 25.

Cho, S. et al., Engineering of Volume-Stable Adipose Tissues, Biomaterials, 2005, pp. 3577-3585, 26.

Kim, B. et al., Tissue Engineering of Smooth Muscle Under a Mechanically Dynamic Condition, J Microbiology & Biotechnology, 2003, pp. 841-845, 13.

Ekholm, M. et al., Tissue Reactions of Subcutaneously Implanted Mixture of epsilon-caprolactone-lactide Copolymer and Tricalcium Phosphate, J Mater Sci: Mater Med, 2003, pp. 913-918, 14.

Jaiswal, N. et al., Osteogenic Differentiation of Purified, Culture-Expanded Human Mesenchymal Stem Cells in vitro, J Cellular Biochemistry, 1997, pp. 295-312, 64.

Lewandrowski, K. et al., Enhanced Bioactivity of a Poly(propylene fumarate) Bone Graft Substitute by Augmentation With Nano-hydroxyapatite, Bio-Medical Mater Eng, 2003, pp. 115-124, 13.

Ginebra, M. P. et al., Effect of the Particle Size on the Micro and Nanostructural Features of a Calcium Phosphate Cement: a Kinetic Analysis, Biomaterials, 2004, pp. 3453-3462, 25.

Burg, K. J. L. et al., Biomaterial Developments for Bone Tissue Engineering, Biomaterials, 2000, pp. 2347-2359, 21.

Akao, M. et al., Mechanical Properties of Sintered Hydroxyapatite for Prosthetic Applications, J Mater Sci, 1981, pp. 809-812, 16.

Anselme, K., Osteoblast Adhesion on Biomaterials, Biomaterials, 2000, pp. 667-681, 21.

Howe, A. K. et al., Anchorage-Dependent ERK Signaling—Mechanisms and Consequences, Current Opinion in Genetics & Development, 2002, pp. 30-35, 12.

Bigi, A. et al., Bonelike Apatite Growth on Hydroxyapatite-gelatin Sponges From Simulated Body Fluid, J Biomed Mater Res, 2001, pp. 709-715, 59.

Vandiver, J. et al., Nanoscale Variation in Surface Charge of Synthetic Hydroxyapatite Detected by Chemically and Spatially Specific High-Resolution Force Spectroscopy, Biomaterials, 2005, pp. 271-283, 26.

Lu, H. H. et al., Three-dimensional, Bioactive, Biodegradable, Polymer-bioactive Glass Composite Scaffolds With Improved Mechanical Properties Support Collagen Synthesis and Mineralization of Human Osteoblast-like Cells in vitro, J Biomed Mater Res, 2003, pp. 465-474, 64.

Li, H. et al., Preparation and Characterization of Bioactive and Biodegradable Wollastonite/poly(D,L-lactic acid) Composite Scaffolds, J Mater Sci: Mater Med, 2004, pp. 1089-1095, 15.

Nayab, S. et al., Adhesion of Bone Cells to Ion-Implanted Titanium, J Mater Sci: Mater Med, 2003, pp. 991-997, 14.

Reis, R. L. et al., Bioenert, Biodegradable and Injectable Polymeric Matrix Composites for Hard Tissue Replacement: State of the Art and Recent Developments, Composites Science and Technology, 2004, pp. 789-817, 64. (Abstract Only).

Whitson, S.W. et al., Factors Influencing Synthesis and Mineralization of Bone Matrix from Fetal Bovine Bone Cells Grown in vitro, J Bone Miner Res, 1992, pp. 727-741, 7. (Abstract Only).

Stupp, S. I. et al., Organoapatites: Materials for Artificial Bone. I. Synthesis and Microstructure, J Biomed Mater Res, 1992, pp. 169-183, 26. (Abstract Only).

\* cited by examiner

PLGA/HYDROXYAPATITE COMPOSITE BIOMATERIAL BY GAS BUBBLE FORMATION

This application claims priority to provisional Application No. 60/767,137 filed on Mar. 6, 2006, the contents of which are expressly incorporated by reference.

SUMMARY OF THE INVENTION

This invention is a novel biomaterial that is especially useful in tissue engineering applications involving bone. It is a composite of poly(D,L-lactic-co-glycolic acid) (PLGA) and nano-sized hydroxyapatite, wherein the hydroxyapatite is highly exposed on the biomaterial surface. A further embodiment of this invention involves a ceramic, such as apatite, that is fastly, highly, and uniformly coated on the biomaterial surface. This new biomaterial is advantageous because it promotes bone cell propagation and ingrowth better than current materials.

BACKGROUND

The ideal bone graft would replace bone defects, such as those from disease or trauma, with a material that allows bone cells to grow into the affected area, thus restoring the bone to its original condition. Currently, autografts are the best material for bone repair because they are biocompatible and there is little risk of disease transfer. However, the downside of autografts is that a separate operation must be performed to remove the person's own bone. Allografts, which consist of bone from another person/cadaver, are also available but carry the risk of immune response and disease transfer that could lead to ultimate failure.

In order to solve the problems associated with bone grafts, many researchers have tried to develop artificial substances for bone grafts. These artificial biomaterials need to possess several qualities in order to be successful. First, the material must be degradable to allow room for new bone to grow into the implant site. Second, it must maintain mechanical strength similar to native bone. Finally, the artificial biomaterial needs to be osteoconductive; that is, it must allow bone cells to attach and propagate on its surface.

Some of the materials that have shown promise as bone grafts include calcium phosphate ceramics such as hydroxyapatite and tricalcium phosphate. These particular ceramics are quite biocompatible because they have characteristics similar to native bone mineral. However, they are hard to shape and do not possess the same mechanical properties as bone. Hydroxyapatite in particular does not degrade quickly either, which inhibits new bone from forming.

Another type of material that has sparked some interest is degradable polymer. It is easy to shape and it degrades at a predictable rate, thereby allowing new bone growth to replace it. Some examples of degradable polymers are poly(glycolic acid), poly(L-lactic acid), and poly(D,L-lactic-co-glycolic acid). Although they are easily formed and have good mechanical strength, degradable polymers alone are not ideal for bone grafts because they are not very osteoconductive. New bone will not attach well or grow well into this material.

It is possible to make a composite using a phosphate ceramic in conjunction with a degradable polymer. Small particles of ceramic can be included within the polymer scaffold material. These particles will be partially exposed on the surface of the biomaterial, thereby making the material more osteoconductive.

Most related methods for making a polymer/ceramic scaffold biomaterial use organic solvents. This can be highly disadvantageous because some residual solvent may remain in the material. Almost all organic solvents are detrimental to cell and tissue growth. Also, it has been noted that these processes may actually leave behind a thin film of polymer that coats the ceramic particles that are supposed to be exposed on the surface. This unintentional thin film disrupts the osteoconductive nature of the ceramic portion of these biomaterials.

The invention disclosed herein addresses these problems by describing a polymer/ceramic biomaterial comprised of degradable polymer and ceramic wherein the ceramic is highly exposed on the surface of the biomaterial and the biomaterial is fabricated with no use of organic solvents. Furthermore, an additional layer of a mineral, such as apatite, can be coated on the surface of the biomaterial in an adherent, fast, uniform fashion. Finally, granules of the polymer/ceramic biomaterial with additional ceramic coating can be fabricated.

All references cited within this application are expressly incorporated by reference in their entirety.

BRIEF SUMMARY OF THE INVENTION

A preferred embodiment of the present invention is a biomaterial comprised of poly(D,L-lactic-co-glycolic acid) (PLGA), hydroxyapatite, and a possible coating of apatite. It is suitable as an artificial bone graft material. The said biomaterial is formed using a gas foaming particle leaching (GF/PL) method. GF/PL introduces gas bubbles into the polymer matrix by saturating the polymer with gas at high pressure, and then reducing the pressure back to ambient conditions. In this case $CO_2$ gas is used. Then, salt particles are leached out of the matrix using distilled water. Both gas foaming and particle leaching leave behind voids, which form the pores of this biomaterial matrix.

The preferred embodiment is made by combining particles of PLGA, hydroxyapatite, and sodium chloride in certain ratios and then using the GF/PL method. The size and amount of each particle will determine the general and interconnected porosity of the final biomaterial. Initially the PLGA, hydroxyapatite, and sodium chloride particles are sieved to obtain particles with a specific size. Then these particles are combined in certain ratios and loaded into a disk mold. The mixture is compressed at a high pressure (around 2000 psi) for about 1 minute. It is believed that pressures as low as 1000 psi and as high as 4000 psi will also work. The resulting disk is then exposed to high pressure $CO_2$ gas (around 800 psi) for 48 hours. It is believed that pressures as low as 400 PSI and as high as 1600 psi will also work. During this time, the $CO_2$ saturates the disk. After 48 hours, the $CO_2$ gas pressure is decreased to ambient pressure. This process leads to nucleation and growth of $CO_2$ pores within the polymer scaffold portions of the biomaterial disk. The sodium chloride particles are subsequently leached out of the material by immersing the disk in distilled water for a lengthy period of time, thus leaving voids formerly occupied by the sodium chloride particles. The final material is highly porous with hydroxyapatite particles exposed on the surface of its polymer network.

Furthermore, coating the surface of the PLGA/hydroxyapatite scaffold with a bone-like apatite using a biomimetic process can increase its osteogenic potential. This biomimetic process involves soaking the biomaterial in a solution of simulated body fluid (SBF) that has appropriate concentrations of ions dissolved in solution. Certain ions will precipitate on the surface of the biomaterial and form an apatite mineral coating.

In another embodiment, the PLGA/hydroxyapatite biomaterial may be ground up and sieved to collect granules with a certain size. These granules may then be soaked in the SBF and receive the apatite coating that enhances its osteogenic properties.

A bone graft material according to the present teachings can be provided in the form of a bone paste, a shaped solid, or a dry pre-mix useful for forming such a paste or solid. The phrase "bone paste" refers to a slurry or semi-solid composition of any consistency that hardens to form a solid structure, and thus includes, e.g., bone plasters, putties, adhesives, cements, bone void fillers, and bone substitutes. As a result, the bone paste can be any composition capable of being injected, molded, painted, suffused, or placed into contact with a bone surface in vivo. The "shaped solid" can take any form, including a pellet that can be placed into a bone void or into contact with a bone surface in vivo. The dry pre-mix can be provided in the form of a powdered and/or granular material.

BRIEF DESCRIPTION OF THE DRAWINGS

FIG. 17 (C) Gross view of the cranium containing the GF/PL HA scaffold.

DESCRIPTION OF THE INVENTION

Figure 1A:
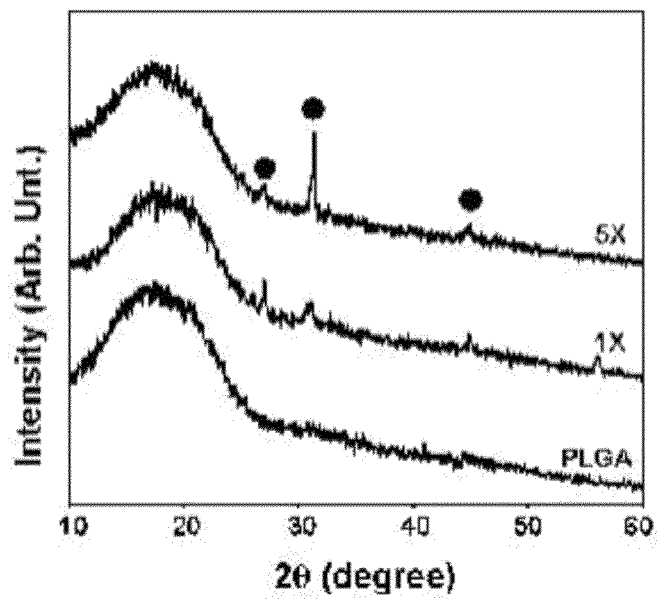
FIG. 1. XRD patterns of apatite-coated (A) PLGA and (B) PLGA/HA scaffolds that were incubated in 1× and 5×SBF for five days.

The present invention is a novel biomaterial with special characteristics that allow it to perform well as a bone graft material. It is comprised of a degradable poly(D,Llactic-co-glycolic acid) polymer scaffolding with incorporated, nano-sized hydroxyapatite particles made by a gas foaming and particle leaching (GF/PL) method. A further embodiment of this invention describes the same biomaterial with an adherent, highly uniform apatite coating.

The method of constructing a PLGA polymer scaffold using GF/PL is described thoroughly in the journal article titled, "*Open pore biodegradable matrices formed with gas foaming*" (Harris L D, Kim B S, and Mooney D J; J Biomed Mater Res, 42, 396-402, 1998). This entire article is hereby incorporated by reference. The research reported in this article found that the porosity and pore size of the PLGA scaffold can be controlled by the salt/PLGA ratio and respective particle sizes. Also, the pores of the matrix are interconnected and highly uniform. In this manner, a useful scaffold can be created without the use of organic solvents or high temperatures.

Although the method for constructing a polymer scaffold using GF/PL is already known, the addition of nano-sized hydroxyapatite particles to this specific polymer scaffolding has not been taught in the prior art. An article has recently been published by the inventor of this application. It describes the addition of hydroxyapatite particles to the PLGA scaffold. It is called, Poly(lactide-co-glycolide)/hydroxyapatite composite scaffolds for bone tissue engineering (Kim S S, Park M S, Jeon O, Choi C Y, and Kim B S; Biomaterial, 27, 1399-1409, available online Oct. 5, 2005). This article is also hereby incorporated by reference. It is important to note that this article is not by another. Students of Dr. Byung-Soo Kim, the sole inventor of the present invention, conducted the research for the article, but the ideas for the invention are uniquely those of Dr. Byung-Soo Kim The research describes how porous PLGA/HA composite scaffolds were fabricated by the modification of the previously described GF/PL method (Harris L D, Kim B S, and Mooney D J; J Biomed Mater Res, 42, 396-402, 1998). The most significant modification of the previous method is the non-obvious addition of nano-sized hydroxyapatite particles that end up being highly exposed on the polymer surface. It is not obvious to one of ordinary skill in the art to add nano-sized hydroxyapatite particles to the polymer matrix and to expose the hydroxyapatite particles on the polymer surface.

PLGA/HA composites were prepared with 75:25 PLGA particles (diameter=100-200 Pm, molecular weight=100,000 Da, Birmingham Polymers, Birmingham, Ala.), HA nanoparticles (diameter=approximately 100 nm, Berkeley Advanced Biomaterials Inc., Berkeley, Calif.), and sodium chloride particles (diameter=100-200 Pm, Sigma, St. Louis, Mo.). The PLGA pellets were ground using a Tekmar grinder (Bel-Art Products, Pequannock, N.J.) and sieved to obtain particles ranging from 100 to 200 Pm. The salt particles were sieved to yield a range of sizes from 100 to 200 Pm. The polymer particles were mixed with the HA and NaCl particles. The PLGA/HA/NaCl mass ratio was 1:1:9. The mixture was loaded into a disk mold (diameter=1.35 cm; Aldrich Chemical Co., Milwaukee, Wis.) and compressed at 2000 psi for 1 min using a Carver Laboratory Press (Fred S. Carver, Inc., Menominee Falls, Wis.) to yield solid disks with a thickness of about 1.7 mm. The samples were then exposed to high pressure $CO_2$ gas (800 psi) for 48 hours to saturate the polymer with the gas. Then, decreasing the gas pressure to ambient pressure created a thermodynamic instability. This led to the nucleation and growth of $CO_2$ pores within the polymer scaffolds. The sodium chloride particles were subsequently removed from the scaffolds by leaching the scaffolds in distilled water for 48 hours.

While the above materials are preferred, it is believed that the present invention will work with polymers of diameters from 50-400 Pm and with HA particles having diameters of 50-200 Pm and salt particles having diameters from 50-300 Pm. It is believed that the ratios of polymer to hydroxy apatite to NaCL can vary by as much as 50% without deviating from the spirit of this invention.

The process for creating these PLGA/HA composite biomaterials can be summarized by the steps of: (1) grinding PLGA to small particles, (2) sieving the PLGA and sodium chloride particles to yield particles with a 100-200 Pm diameter, (3) mixing the particles PLGA/HA/NaCl in a mass ratio of 1:1:9, (4) loading the mixture of particles into a disk mold, (5) compressing the mixture with a very high pressure for a certain amount of time, (6) exposing the newly formed disk to high pressure $CO_2$ gas long enough to saturate the disk, (7) decreasing the pressure on the disk until it returns to ambient pressure, (8) soaking the disk in distilled water to dissolve and leach out the sodium chloride particles.

A further embodiment of the invention involves forming a uniform mineral coating of apatite on the surface of the PLGA/hydroxyapatite biomaterial. This apatite layer enhances the osteogenic potential of the biomaterial scaffold.

The apatite layer is created by incubating the scaffolds in an ion rich simulated body fluid (SBF) solution. The solution is prepared by dissolving reagent grade NaCl, $NaHCO_3$, $Na_2SO_4$, KCl, $K_2HPO_4$, $MgCl_2.6H_2O$, and $CaCl_2.2H_2O$ in distilled deionized water. 1×SBF has the same ion concentrations as blood plasma while 5×SBF has ion concentrations five times greater than blood plasma. The pH is adjusted to 6.4 with tris(hydroxymethyl)aminomethane.

The described PLGA/hydroxyapatite biomaterial can be coated with apatite relatively quickly because the exposed hydroxyapatite particles act as nucleation sites for the growth of the mineral apatite layer in SBF solution. Although the method for coating of polymeric biomaterial with apatite by incubating the biomaterial in SBF solution is already known, accelerated coating by incubating polymeric biomaterial with nano-hydroxyapatites exposed on the biomaterial surface has not been taught in the prior art. A study was conducted to compare the formation of an apatite layer on both PLGA and PLGA/nanohydroxyapatite scaffolds created by the GF/PL method. Each was incubated in 1× and 5×SBF for up to five days. A series of brief evacuation-repressurization cycles were performed to force the solution into the pores of the scaffold. The SBF was refreshed every day. After various incubation times the samples were removed, rinsed, and dried in vacuum before being characterized.

Figure 1B:
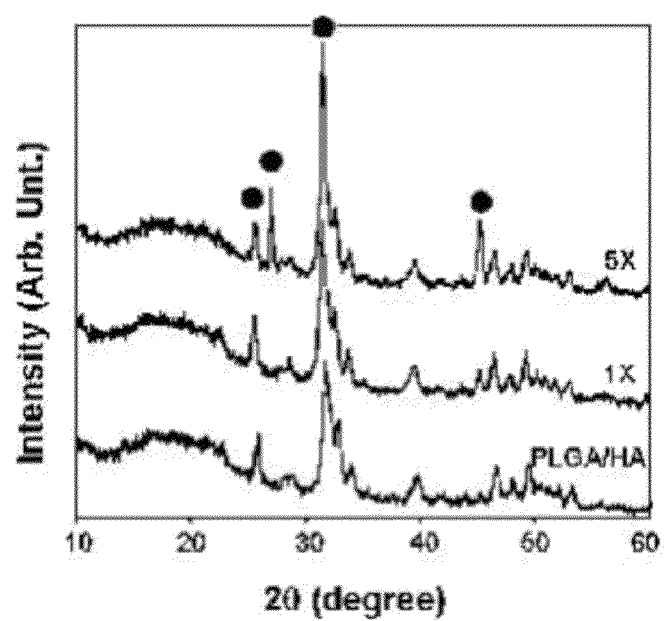

The PLGA and PLGA/nano-hydroxyapatite specimens were characterized. The morphologies of the scaffolds were examined by scanning electron microscopy (SEM; JSM6330F, JEOL, Tokyo, Japan) after platinum coating. X-ray diffraction (XRD) spectra were obtained using an X-ray diffractometer (D/MAX-2500, Rigaku Co., Tokyo, Japan) with a mixed incidence of 1° and a 2Θ scanning rate of 2.5°/min in the range of 10-60°. Cu Kα radiation, with a voltage of 40 kV and a current of 100 mA, was used for the diffraction. The XRD results are shown in FIG. 1. It is apparent that the PLGA/hydroxyapatite results show the higher intensity peaks expected from greater apatite formation on the PLGA/hydroxyapatite composite biomaterial.

Figure 2A:
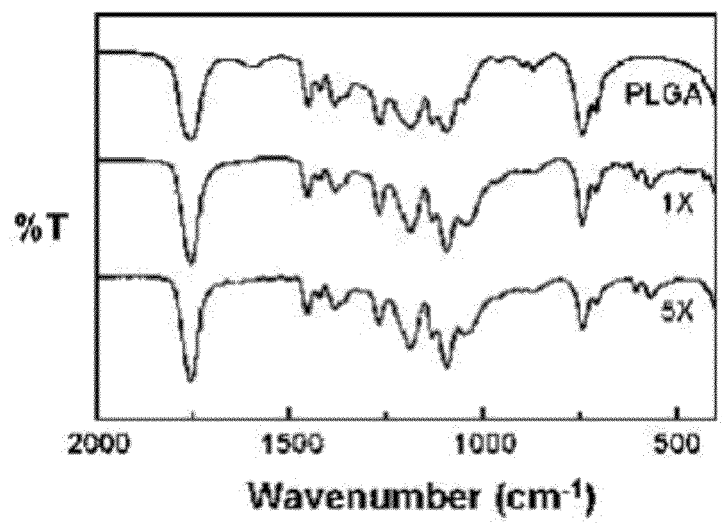
FIG. 2. FT-IR spectra of apatite-coated (A) PLGA and (B) PLGA/HA scaffolds that were incubated in 1× and 5×SBF for five days.
Figure 2B:
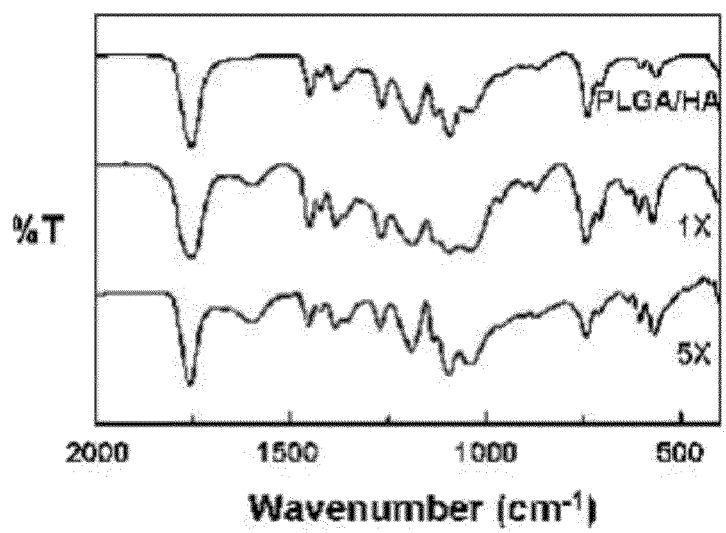

Fourier transformed infrared spectroscopy (FT-IR) spectra were obtained using a FT-IR spectrometer (Avatar 360, Nicolet Instrument Corp., Madison, Wis., USA) with a resolution of 8 cmil. For FT-IR analysis, the scaffolds were cut into fine particles, milled with potassium bromide, and pressed into transparent thin discs. The scaffold mass increase during apatite formation in SBF was measured using an analytical balance accurate to 10-4 g (EPG214C, Ohaus Corp., Pine Brook, N.J., USA), and the data is shown in FIG. 2.

Figure 3:
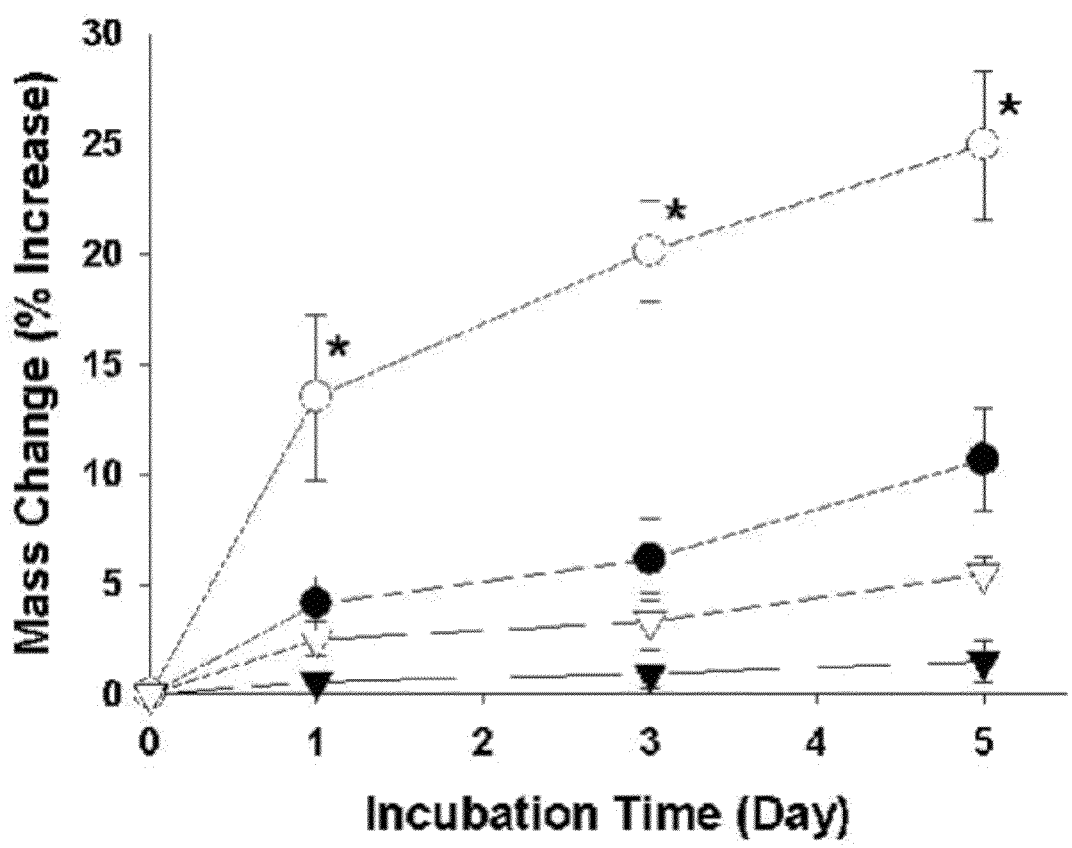
FIG. 3. The mass change of apatite-coated PLGA (inverted triangle) and PLGA/HA (circle) scaffolds incubated in 1× (solid) and 5×SBF (open) for various time periods. The mass change was expressed as the percent increase compared to the mass of scaffolds incubated in a tris-buffer solution for identical times. The initial mass was identical for both types of scaffolds with *P<0.05 compared to the other groups.

Finally, the scaffolds were air-dried and then vacuum dried. The mass increase from apatite formation was expressed as a percent increase compared to the scaffold mass when incubated in a tris-buffer at the same pH value, at the same temperature, and for the same time intervals. The data in FIG. 3 shows that the PLGA/hydroxyapatite scaffolds (circles) gained the greatest mass due to apatite formation. Furthermore, it is also evident that SBF solutions with higher ion concentrations lead to greater apatite deposition.

SEM micrographs of the apatite coated PLGA samples revealed that the apatite layer was not uniform. There were areas of bare PLGA, which shows that there was poor apatite deposition. However, the PLGA/hydroxyapatite scaffolds showed a more desirable, uniform apatite layer.

More significantly, the apatite-coated PLGA/hydroxyapatite scaffolds exhibited noticeably improved cell growth and mineralization, when seeded with osteoblast cells, compared with apatite-coated PLGA scaffolds in vitro. This result supports the hypothesis that the uniform apatite layer is favorable for osteogenic properties.

The biomimetic apatite coating process is enhanced by introducing nano-sized hydroxyapatite nucleation sites and by using concentrated SBF solution. This coating is advantageous because it conveys better osteogenic properties to the PLGA/hydroxyapatite biomaterial.

A further embodiment of this invention involves the coating of PLGA/nanohydroxyapatite particles (rather than scaffolds) with a biomimetic, adherent, and uniform apatite coating. The particles may be the product of a reaction process or be ground down from bulk PLGA/nano-hydroxyapatite composite to a size of 30-2000 Pm. The particles will be sieved to isolate particles with a more narrow size distribution depending on the desired application. These particles will then be soaked in SBF solution to coat them with a uniform layer of biomimetic apatite.

Most of the previous methods for fabricating polymer/bioceramic composite scaffolds, such as the solvent casting and particulate leaching (SC/PL) method or the phase separation method, use organic solvents. However, residual solvents in the scaffolds may be harmful to transplanted cells or host tissues. Furthermore, the polymer coating on the ceramics created by polymer solutions may hinder the exposure of the ceramics to the scaffold surfaces (FIG. 4A), which could decrease the chance that osteogenic cells make contact with the bioactive ceramics.

The preferred embodiment of the present invention relies on gas forming and particulate leaching (GF/PL) methods to fabricate PLGA/HA composite scaffolds for bone tissue engineering. This method efficiently exposes the bioceramic on the scaffold surfaces and avoids the use of organic solvents. To reduce the amount of HA (which degrades extremely slowly in vivo) required, and to increase the HA exposure to the scaffold surface, HA particles approximately 100 nm in size rather than micro-sized particles, are used to fabricate the composite scaffolds. The HA exposure at the scaffold surface in GF/PL scaffolds was compared to that in SC/PL scaffolds see FIGS. 4 A-C.

EXAMPLE 1

Porous PLGA/HA composite scaffolds were fabricated by the modification of a previously described GF/PL method of 24. Harris L D, Kim B S, Mooney D J. *Open pore biodegradable matrices formed with gas foaming*. J Biomed Mater Res 1998; 42: 396-402. PLGA/HA composites were prepared with 75:25 PLGA particles (diameter=100-200 mm, molecular weight=100,000 Da, Birmingham Polymers, Birmingham, Ala.), HA nanoparticles (diameter=approximately 100 nm, Berkeley Advanced Biomaterials Inc., Berkeley, Calif.), and sodium chloride particles (diameter=100-200 mm, Sigma, St. Louis, Mo.). The PLGA pellets were ground using a Tekmar grinder (Bel-Art Products, Pequannock, N.J.) and sieved to obtain particles ranging from 100 to 200 mm. The salt particles were sieved to yield a range of sizes from 100 to 200 mm. The polymer particles were mixed with the HA and NaCl particles. The PLGA/HA/NaCl mass ratio was 1:1:9. The mixture was loaded into a disk mold (diameter=1.35 cm; Aldrich Chemical Co., Milwaukee, Wis.) and compressed at 2000 psi for 1 min using a Carver Laboratory Press (Fred S. Carver, Inc., Menominee Falls, Wis.) to yield solid disks with a thickness of 1.7 mm. The samples were then exposed to high pressure CO2 gas (800 psi) for 48 h to saturate the polymer with the gas. Then, decreasing the gas pressure to ambient pressure created a thermodynamic instability. This led to the nucleation and growth of CO2 pores within the polymer scaffolds. The NaCl particles were subsequently removed from the scaffolds by leaching the scaffolds in distilled water for 48 h. PLGA scaffolds without HA were also fabricated by the GF/PL method and used as a control (GF/PL-no HA).

Porous PLGA/HA scaffolds were also fabricated by the modification of a previously described SC/PL methods of Wei G, Ma P X. *Structure and properties of nano-hydroxyapatite/polymer composite scaffolds for bone tissue engineering*. Biomaterials 2004; 25:4749-57; Cho S W, Kim I K, Lim S H, Kim D I, Kang S W, Kim S H, et al. *Smooth muscle-like tissues engineered with bone marrow stromal cells*. Biomaterials 2004; 25:2979-86; Cho S W, Kim S S, Rhie J W, Cho H M, Choi C Y, Kim B S. *Engineering of volume-stable adipose tissues*. Biomaterials 2005; 26: 3577-85; Kim B S, Jeong S I, Cho S W, Nikolovski J, Mooney D J, Lee S H, et al. *Tissue engineering of smooth muscle under a mechanically dynamic condition*. J Microbiol Biotech 2003; 13:841-5, and were used as another control. In this process, PLGA was dissolved in methylene chloride (J. T. Baker, Phillipsburg, N.J.) at a 10% (w/v) concentration, and HA and NaCl were added to the PLGA solution at the same sizes and ratios as for the GF/PL scaffolds. This mixture was loaded into Teflon cylinders (diameter=21.5 mm, height=25 mm; Cole-Parmer Instrument Company, Vernon Hills, Ill.). Following solvent evaporation, the polymer disks with entrapped salt particles were removed from the molds. The salt was removed by immersing disks in distilled water for 48 h.

The porosity of fabricated scaffolds was measured using mercury intrusion porosimetry (Autopore IV 9500, Micromeritics Instrument Corporation, Norcross, Ga.). A contact angle of 1301 for mercury on the scaffold was used for this analysis. The pore structures of the scaffolds were examined using a scanning electron microscope (SEM, JEOL, Tokyo, Japan). Compression and tensile tests were performed with an Instron mechanical tester (Instron 4201, Instrons, Canton, Mass.). The scaffold samples were cut into 1×1 cm2 for compression testing. For tensile testing, the samples (1×1 cm2) were attached to cardboard using epoxy glue. The sample was centered in a 7 mm slot in the center of the cardboard and then glued to standardize the gauge length. Compression and tensile tests were performed with a constant strain rate of 1 mm/min. The moduli were determined from the slopes in the initial elastic portion of the stress-strain diagram. To examine the distribution and extent of surface exposure of HA in the scaffolds, the HA exposed to the scaffold surface was visualized with a hydrophilic dye (trypan blue, Sigma) staining. The residual dye was removed by sonication in 100% ethanol. Afterwards, the surface of the PLGA/HA scaffolds was examined with a microscope (Camscope, Samtech, Seoul, Korea). To examine the chemical composition of the scaffold surface, we carried out X-ray photoelectron spectroscopic (XPS; Sigma Probe, ThermoVG Scientific, West Sussex, UK) analyses, evaluating the O 1s, C 1s, Ca 2p, and P 2p peaks. The residual pressure in the spectrometer was $1.1 \times 10^{-8}$ Pa, and a Mg anode (1.25 keV) powered at 250 W was used as an X-ray source. The constant pass energy was 23 eV. All XPS data were acquired at a nominal photoelectron takeoff angle of 551. The area of the XPS peaks was determined after background subtraction, and the atomic percentage was determined by normalizing the peak area of each element by the total peak areas of all elements.

Osteoblasts were isolated from the calvaria of neonatal (less than one day old) Sprague-Dawley rats (SLC, Tokyo, Japan) by an enzymatic digestive process. The calvaria were isolated, and all connective tissues were carefully removed. The parietal bones were minced into pieces measuring about $1\times1$ mm$^2$ using sterile surgical scissors. Osteoblasts were isolated by an enzyme solution containing 1.37 mg/ml collagenase type I (Sigma) and 0.5 mg/ml trypsin (Sigma). Following 30 min of incubation, the released cells were discarded to prevent contamination with other cell types. The minced bones were redigested with the enzyme solution for 30 min, and the supernatant was transferred to the culture medium, Dulbecco's Modified Eagles Medium (DMEM, Gibco BRL, Gaithersburg, Md.) containing 10% (v/v) fetal bovine serum (Gibco BRL), 1% (v/v) penicillin-streptomycin (Gibco BRL), 10 mM b-glycerophosphate (Sigma), 50 mg/ml L-ascorbic acid (Sigma), and 100 nM dexamethasone (Sigma). This process was repeated three times, and then finally the collected solution was centrifuged for 10 min at 1500 rpm. Cells were plated into tissue culture flasks and cultured in a humidified incubator at 37° C. with 5% (v/v) $CO_2$.

The fabricated scaffolds were sterilized by ethylene oxide gas and pre-wetted in the culture medium for 12 h. Aliquots of 50 ml of the cell suspension ($4.0\times10^7$ cells/ml, $2.0\times10^6$ cells/scaffold) were seeded onto the tops of the pre-wetted scaffolds. The scaffolds were left undisturbed in an incubator for 3 h to allow the cells to attach to the scaffolds. An additional 1 and 10 ml of culture medium were added to each scaffold at 6 and 8 h, respectively. The cell/scaffold constructs were cultured in a humidified incubator at 37° C. with 5% (v/v) $CO_2$ for eight weeks. The medium was changed everyday. Analytical assays were performed at 7, 14, 28, and 56 days.

To determine the seeding efficiency and cell growth on the scaffolds, cell numbers were determined by quantitative DNA assays (n=3). DNA was isolated using a Wizard Genomic DNA Purification kit (Promega, Madison, Wis.). For DNA isolation, the cell/scaffold constructs were washed twice with phosphate-buffered saline. The specimens were placed in a 1.5-ml tube and crushed with a homogenizer (PowerGen 125, Fisher Scientific, Germany). DNA was isolated according to the kit protocol, and DNA content was measured with an ultraviolet absorbance spectrophotometer (JASCO V-530, Tokyo, Japan) at 260 nm. The cell numbers were calculated from a DNA standard curve of identical cells.

The alkaline phosphatase (ALP) production of osteoblasts cultured on scaffolds was measured spectroscopically (n=3) using the methods of Ekholm M, Hietanen J, Tulamo R M, Muhonen J, Lindqvist C, Kellomaki M, et al. *Tissue reactions of subcutaneously implanted mixture of epsilon-caprolactone-lactide copolymer and tricalcium phosphate. An electron microscopic evaluation in sheep*. J Mater Sci Mater Med 2003; 14:913-8. The osteoblast/scaffold constructs were washed with PBS, homogenized with 1 ml Tris buffer (1 M, pH 8.0, Sigma), and sonicated for 4 min on ice. Aliquots of 20 ml were incubated with 1 ml of a p-nitrophenyl phosphate solution (16 mM, Sigma) at 30 1 C. for up to 5 min. The production of p-nitrophenol in the presence of ALP was measured by monitoring light absorbance at 405 nm.

The amount of calcium deposited in the cell-scaffold constructs was measured using a previously reported method (n=3) of Jaiswal N, Haynesworth S E, Caplan A I, Bruder S P. *Osteogenic differentiation of purified, culture-expanded human mesenchymal stem cells in vitro*. J Cell Biochem 1997; 64:295-312. After the cell-scaffold constructs were rinsed twice with PBS and homogenized with 0.6 N HCl, calcium was extracted by shaking for 4 h at 4° C. The lysate was then centrifuged at 1000 g for 5 min, and the supernatant was used to determine calcium content. To measure the amount of calcium produced by the seeded osteoblasts, the calcium content of the PLGA/HA scaffold itself was also measured, and the calcium content of the scaffold itself was subtracted from the total calcium content of the lysate. The calcium concentration in the cell lysates was quantified spectrophotometrically with cresolphthalein complexone (Sigma). Three minutes after the addition of reagents, the absorbance of the samples was read at 575 nm using a microplate reader (Multiskan Spectrum, Thermo Electron Co., Vantaa, Finland). The calcium concentration was calculated from a standard curve generated from a serial dilution of a calcium standard solution (Sigma).

The surface and cross-sectional morphologies of the scaffolds and cell-scaffold constructs were examined using a SEM. The samples were washed twice with PBS, prefixed in 1% (v/v) buffered glutaraldehyde for 1 h, and fixed in 0.1% (v/v) buffered formaldehyde for 24 h. The fixed samples were dehydrated in ascending grades of ethanol, dried, and mounted on aluminum stubs using double-sided carbon tape. The specimens were coated with gold using a Sputter Coater (Cressington 108, Cressington Scientific Instruments, Cranberry, Pa.) and examined with SEM at an acceleration voltage of 10 kV.

In addition to the culture of cell-scaffold constructs in vitro, cell scaffold constructs were implanted into the subcutaneous space of athymic mice (BALB/c-nu, 7 weeks old, female, SLC, Tokyo, Japan). After the mice were anesthetized with an intramuscular administration of ketamine hydrochloride (50 mg/kg, Yuhan Co., Seoul, Korea) and xylazine hydrochloride (5 mg/kg, Bayer Korea Ltd., Seoul, Korea), small incisions were made on the dorsal skins of six mice. Four pouches per animal were made by blunt dissection in subcutaneous sites, and cell-seeded scaffolds were immediately implanted into the pouches (n=4). Subsequently, the skin was closed with 5-0 Vicryl sutures (Ethicon, Lenneke Marelaan, Belgium). The mice were housed singly after surgery and received humane care in compliance with the Hanyang University Guidelines for the care and use of laboratory animals. The implants were retrieved for analysis at five and eight weeks after implantation.

Cell-scaffold constructs were retrieved from athymic mice at five and eight weeks after implantation (FIG. 8B), fixed in 10% (v/v) buffered formaldehyde, dehydrated in ascending grades of ethanol, and embedded in paraffin. The tissue blocks were sectioned at a 4-mm thicknesses and stained with hematoxylin and eosin (H&E) and Masson's trichrome. The Masson's trichrome-stained mid-portion sections were examined with a microscope for histomorphometry. The percentage of bone occupying space within the constructs was measured using an image analysis system (KS400, Zeiss, Munich, Germany) coupled to a light microscope. The bone formation area was expressed as the percentage of bone area in the available pore space (bone area/pore area×100%).

Quantitative data were expressed as the mean standard deviation. Statistical comparisons were carried out using analysis of variance (ANOVA, SAS Institute Inc., Cary, N.C.). A value of $p<0:05$ was considered to be statistically significant.

Figure 4A:
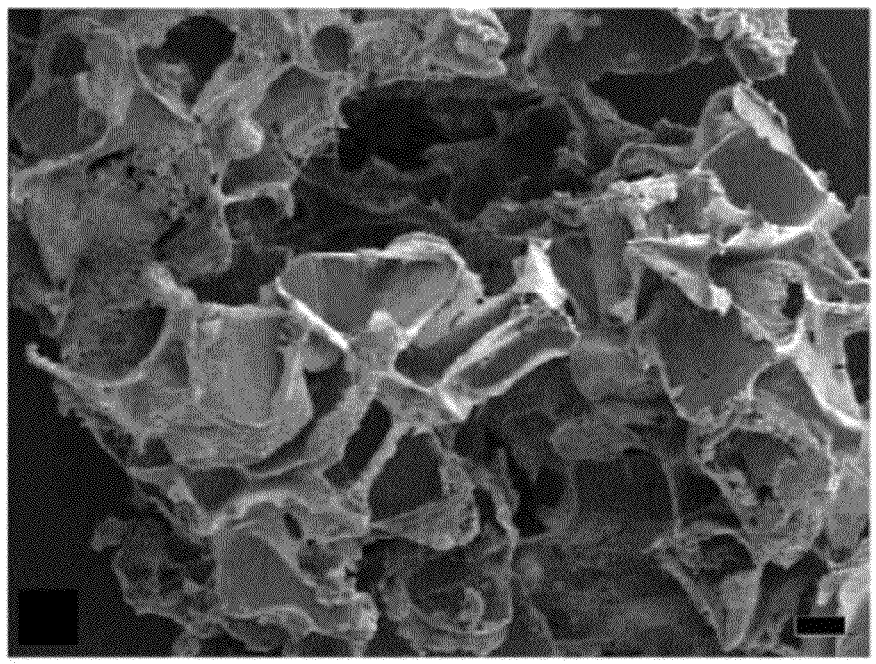
FIGS. 4 (A)-(D) Scanning electron micrographs of (A,C) surfaces and (B,D) cross-sections of the PLGA/HA composite scaffolds fabricated by (A,B) the SC/PL method and (C,D) the GF/PL method.
Figure 4B:
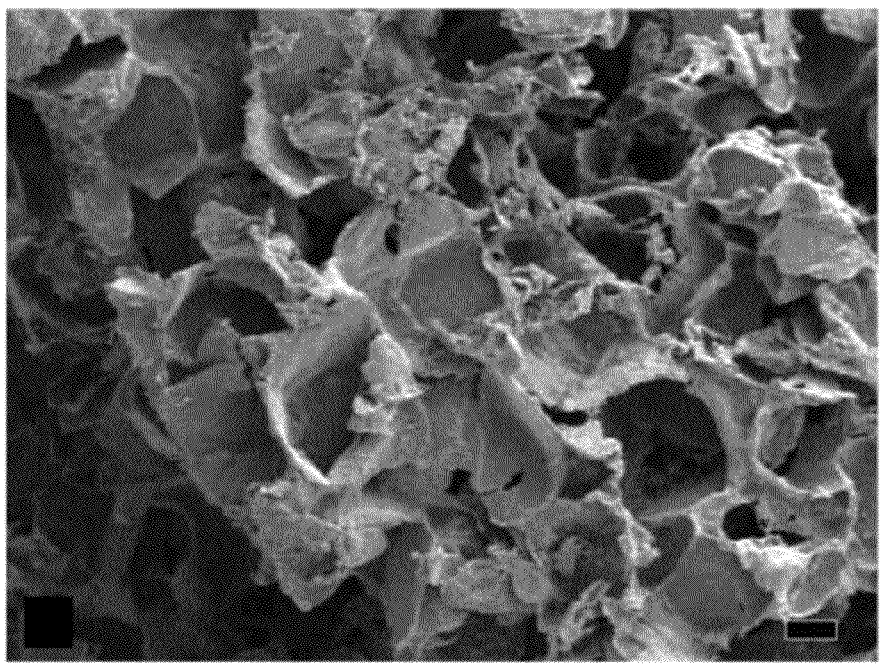
Figure 4C:
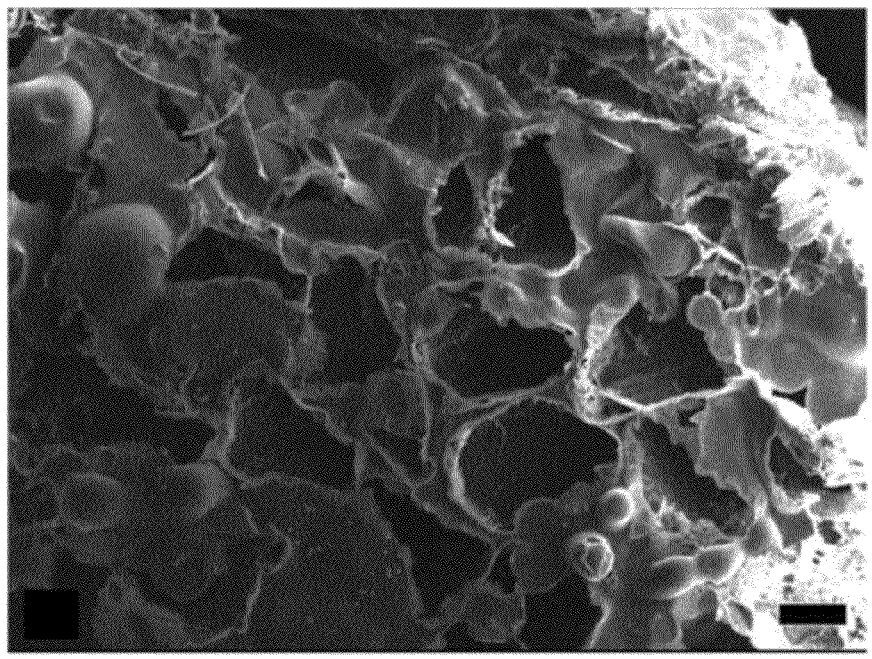
Figure 4D:
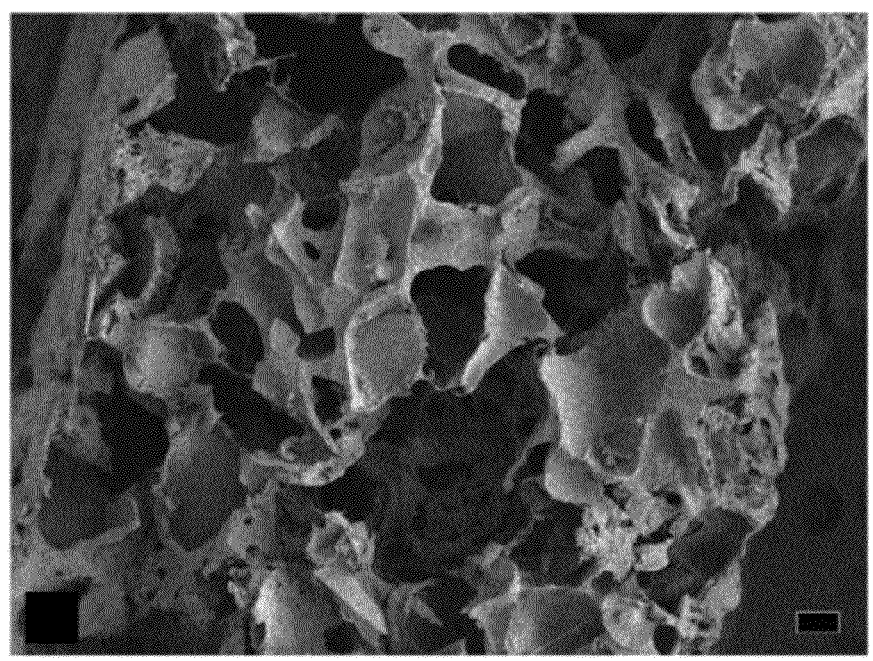
Figure 5A:
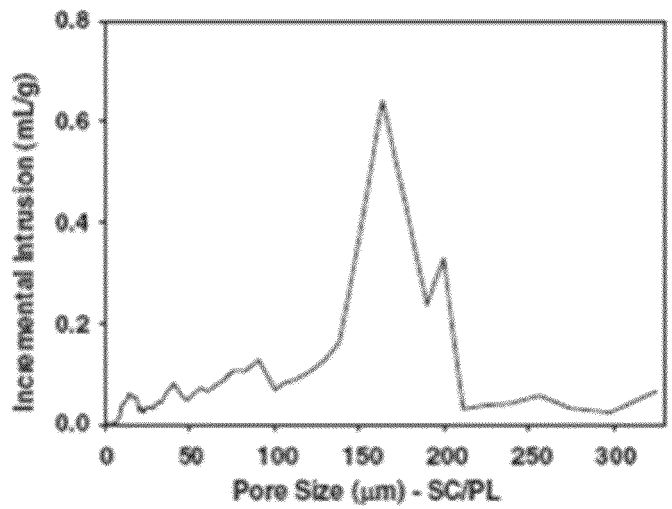
FIGS. 5(A)-(B) Pore size distributions of the: (A) SC/PL and (B) GF/PL scaffolds FIG. 6(A) A macroscopic image of three types of scaffolds FIG. 6(B) Microscopic images of stained GF/PL-no HA scaffold, FIG. 6(C) Microscopic images of stained SC/PL scaffold, FIG. 6(D) Microscopic images of stained GF/PL scaffold.
Figure 5B:
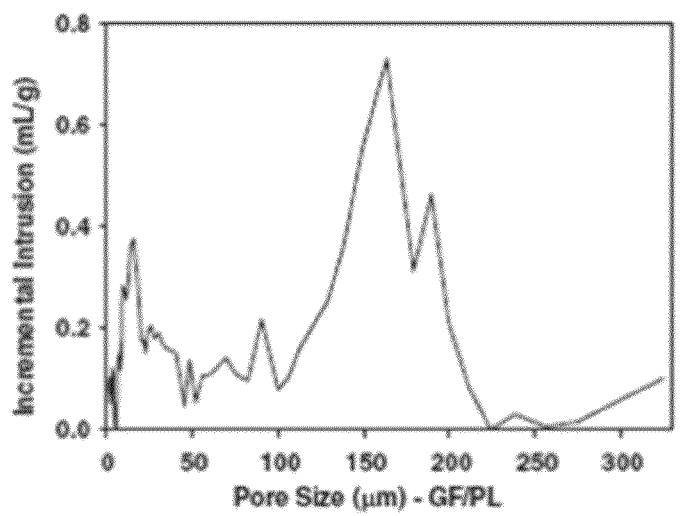

Gas foaming and the subsequent salt leaching of scaffolds containing a high percentage (90%) of NaCl particles (diameter range 100-200 mm) led to the formation of highly porous, open pore structures with no evidence of an external, nonporous skin layer (FIGS. 4C and D). The pore structure observed in the cross-sections of the GF/PL scaffolds was similar to that of the scaffolds fabricated by the SC/PL method (FIGS. 4A and B). The SC/PL method produced scaffolds with pore sizes of approximately 100-200 mm (FIG. 5A). In contrast, the GF/PL process resulted in scaffolds with two levels of porosity: interconnected macropores (100-200 mm) were created by the leaching of the NaCl particles, and smaller, closed pores (10-45 mm) were created by the nucleation and growth of gas pores within the polymer particles (FIG. 5B). The average porosities of the GF/PL and SC/PL scaffolds were 91±3% and 85±3% respectively.

The mechanical properties of the scaffolds were assessed using compressive and tensile mechanical tests. The GF/PL scaffolds exhibited enhanced mechanical properties as compared to the SC/PL scaffolds. The average compressive moduli were 2.3±0.4 and 4.5±0.3 MPa ($p<0:05$) for the SC/PL and GF/PL scaffolds, respectively. The average tensile moduli were 2.0±0.1 and 26.9±0.2 MPa ($p<0:05$) for the SC/PL and GF/PL scaffolds, respectively. These data represent a 99% increase in the compression modulus and a 1331% increase in tensile modulus, demonstrating the positive effects of the GF/PL fabrication process in enhancing the mechanical properties of the scaffolds.

Figure 6A:
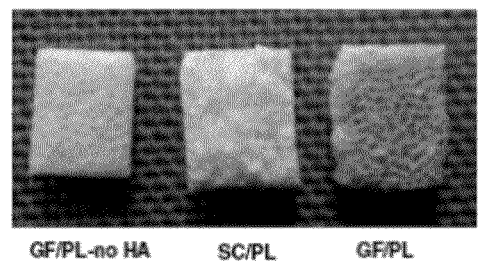
FIG. 6 (E) XPS analyses of SC/PL scaffold
FIG. 6(F) XPS analyses of GF/PL scaffold.
FIG. 6(G) The atomic percentages of calcium exposed to the scaffold surface in GF/PL and SC/PL scaffolds.
Figure 6B:
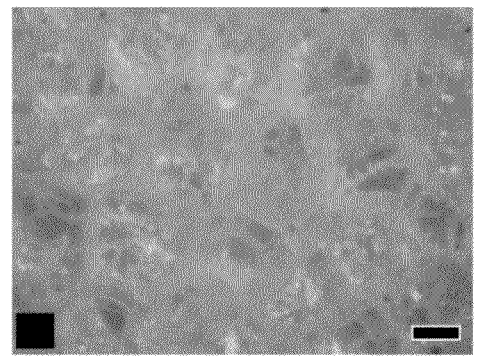
Figure 6C:
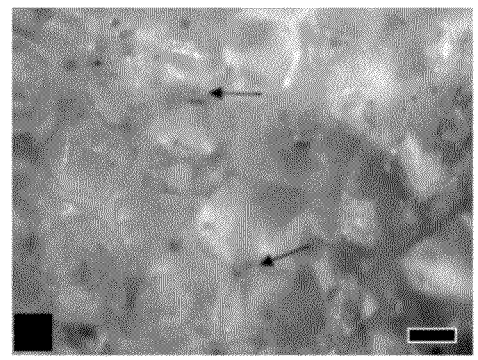
Figure 6D:
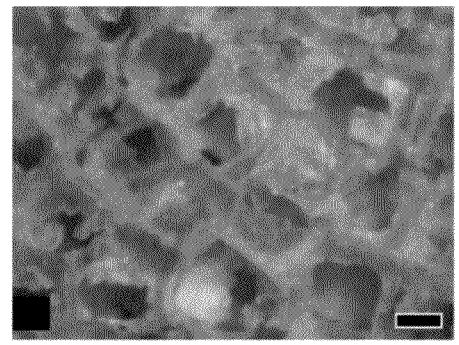
Figure 6E:
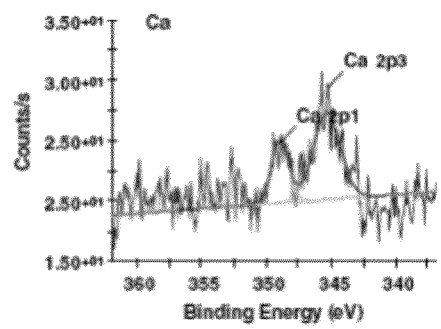
Figure 6F:
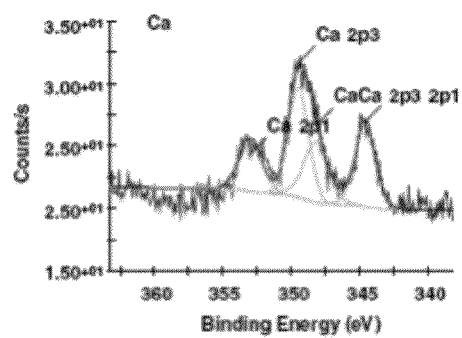
Figure 6G:
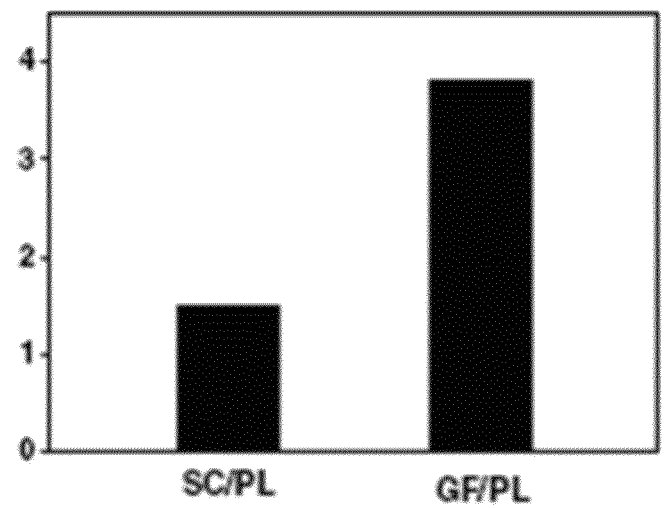

To determine whether the scaffold fabrication process affects the extent of HA exposure at the scaffold surface, the exposed HA was stained with a hydrophilic dye. HA was stained more abundantly in the GF/PL scaffolds than in the SC/PL scaffolds (FIGS. 6A, C and D). The surface composition of the PLGA/HA composite scaffolds was also analyzed with XPS. The amount of Ca in the GF/PL scaffold surface was greater than in the SC/PL scaffold surface (FIGS. 6E and F). The atomic ratio of the Ca exposed on the scaffold surface was 156% higher on the GF/PL scaffold surface compared with the SC/PL scaffold surface (FIG. 6G).

Figure 7A:
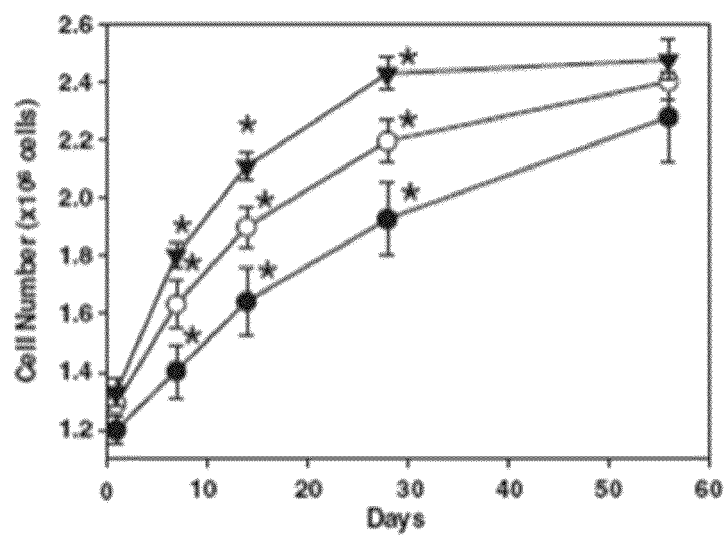
FIGS. 7 (A)-(C) The (A) growth rate, (B) alkaline phosphatase (ALP) activity, and (C) calcium deposition of the osteoblasts cultured on GF/PL (lined bars), SC/PL (blank bars) and GF/PL-no HA (solid bars) scaffolds for eight weeks in vitro.
Figure 8A:
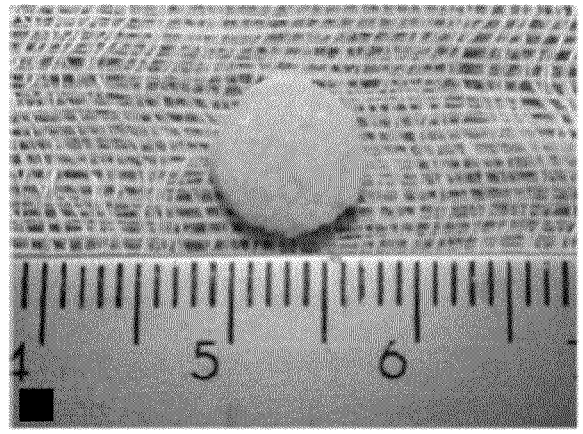
FIGS. 8 (A)-(B) (A) Cell-seeded GF/PL scaffold prior to implantation. The scale is in centimeters. (B) A gross view of cell/scaffold constructs retrieved at eight weeks after implantation to the subcutaneous spaces of athymic FIGS. 9(A)-(D) Histological evaluations of cell/polymer constructs retrieved at five weeks after implantation to the subcutaneous spaces of athymic mice. (A,C) H&E staining and (B,D) Masson's trichrome staining.
Figure 8B:
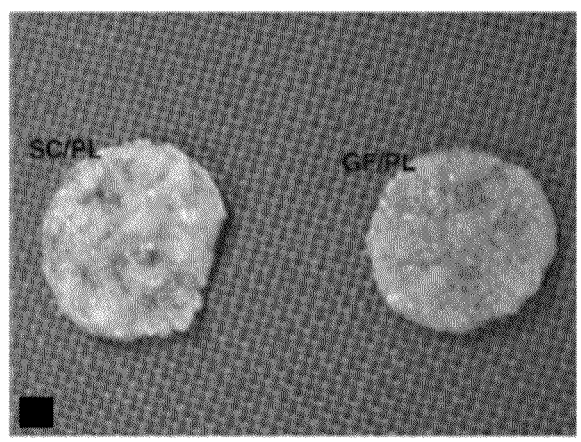

Both types of the PLGA/HA composite scaffolds allowed for the adhesion and proliferation (FIG. 7A) of the seeded rat calvarial osteoblasts over the 56-day in vitro culture period. The initial cell seeding density of $2.00\times106$ cells/scaffold resulted in $1.33\times106$ cells/scaffold remaining attached to the GF/PL scaffold after one day in culture, giving an adhesion percentage of 66.5%. For the SC/PL scaffold, the cell adhesion efficiency was 62.0%. Osteoblasts grew more rapidly in the GF/PL scaffolds than in the SC/PL scaffolds (FIG. 7A). The average cell density of the GF/PL scaffolds was $2.48\times106$ cells/scaffold after four weeks in culture, while that of the SC/PL scaffolds was $2.19\times106$ cells/scaffold, corresponding to 86.5% and 69.7% increases in cell density for the GF/PL and SC/PL scaffolds, respectively (FIG. 8a and FIG. 8b).

Figure 7B:
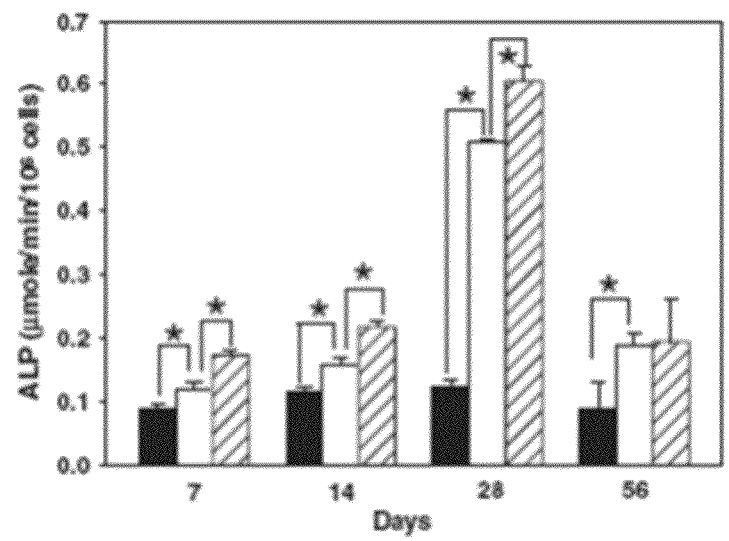

The ALP activity of the osteoblasts cultured on both types of PLGA/HA composite scaffolds increased during the four-week culture period and decreased at eight weeks (FIG. 7B). In contrast, the ALP activity of the osteoblasts grown on the PLGA scaffolds without HA was low and did not show significant changes during the culture period. The osteoblasts on the GF/PL scaffolds showed significantly higher ($p<0:05$) levels of ALP activity compared to the osteoblasts on the SC/PL scaffolds during the first four weeks of culturing, but showed no significant differences at eight weeks.

Figure 7C:
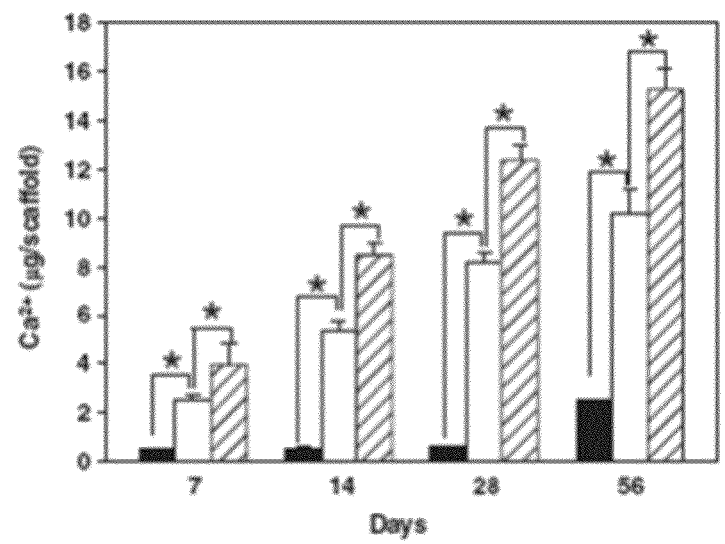

The calcium deposition by cultured osteoblasts was significantly higher ($p<0:05$) on the GF/PL scaffolds than on the SC/PL scaffolds during the 8-week culture period (FIG. 7C). The deposition on both types of the PLGA/HA scaffolds gradually increased during the culture period. On the PLGA scaffolds without HA, calcium deposition was significantly lower than on both types of the PLGA/HA scaffolds. The calcium deposition on the PLGA scaffolds remained constant at low levels for the first four weeks, and increased slightly at eight weeks.

Figure 9A:
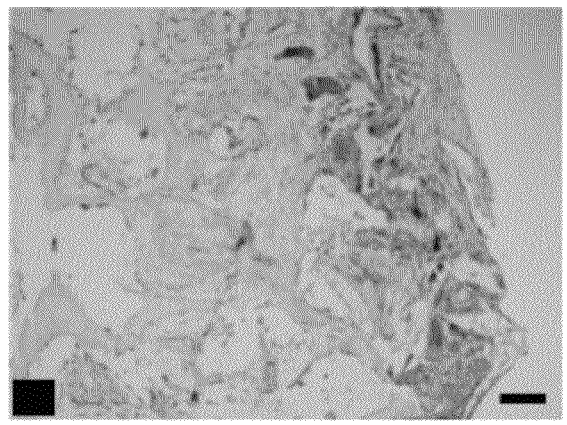
Figure 9B:
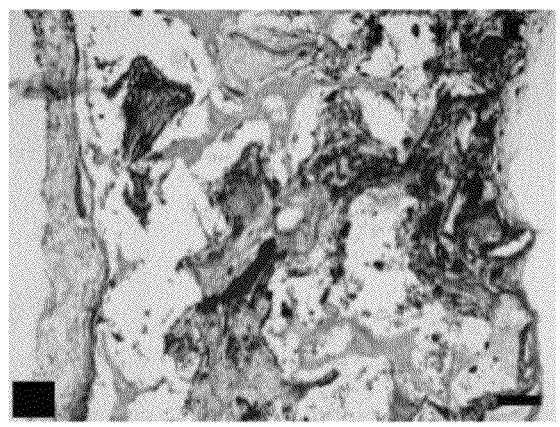
Figure 9C:
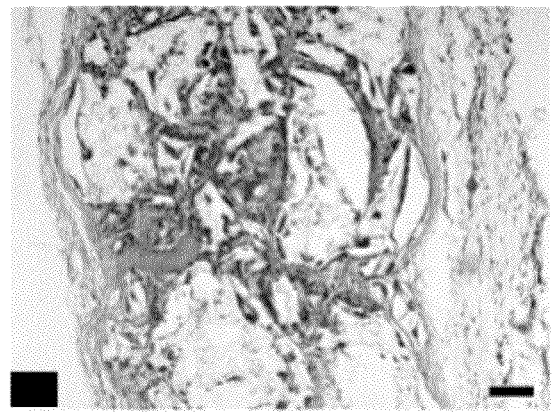
Figure 9D:
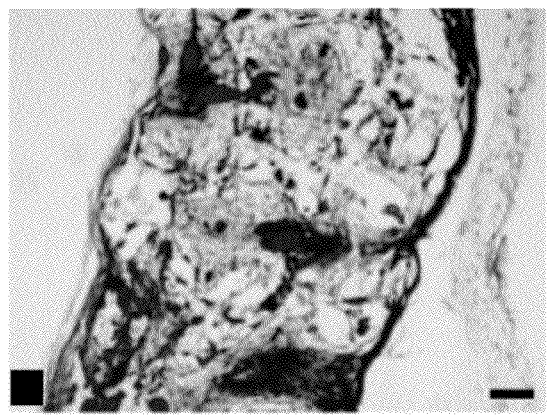
Figure 10A:
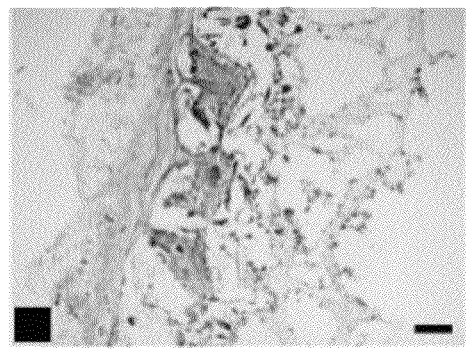
FIGS. 10(A)-(F) Histological evaluations of cell/polymer constructs retrieved at eight weeks after implantation to the subcutaneous spaces of athymic mice. (A,C,E) H&E staining and (B,D,F) Masson's trichrome staining.
Figure 11A:
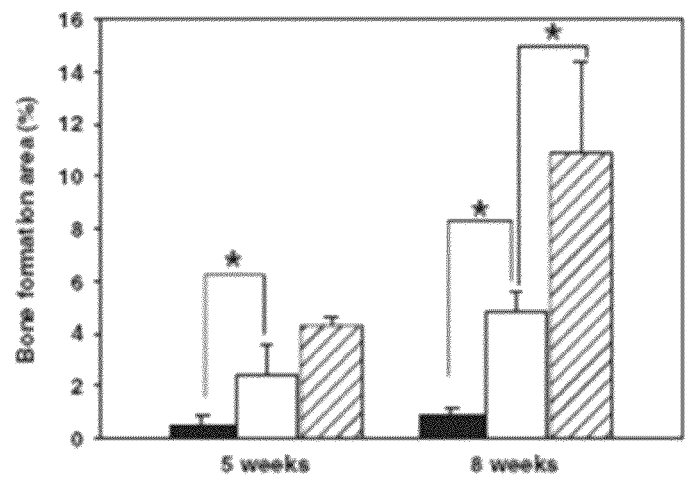
FIG. 11(A)-(B) (A) Bone formation area and (B) calcium deposition in GF/PL (lined bars), SC/PL (blank bars) and GF/PL-no HA (solid bars) scaffolds at eight weeks after implantation.

The implantation of both types of the osteoblast-seeded PLGA/HA composite scaffolds resulted in new bone formation in vivo in ectopic sites at five and eight weeks after implantation. Five weeks after implantation, a small amount of woven bone was detected in both the SC/PL (FIGS. 9A and B) and the GF/PL (FIGS. 9C and D) scaffolds. Eight weeks after implantation, osteogenesis had progressed, and more bone with lamellar structures appeared (FIG. 10C-F). Histomorphometric analyses of the mid-portion sections of the regenerated tissues showed enhanced bone formation in the GF/PL scaffolds, compared with the SC/PL scaffolds and the PLGA scaffolds with no HA, at five and eight weeks after implantation (FIG. 11A). In contrast, the cell-seeded PLGA scaffolds with no HA had produced nearly no new bone in vivo for eight weeks. Most of the pores of the PLGA scaffolds with no HA were filled with loose fibrous connective tissues without evidence of bone formation at five and eight weeks after implantation (FIGS. 10A and B).

Figure 11B:
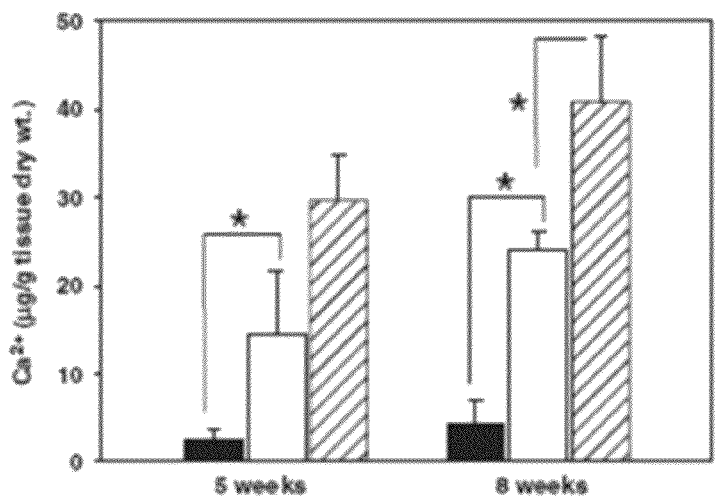

The calcium deposition in the regenerated tissues was much more extensive in the GF/PL scaffold group than in the SC/PL scaffold group at five and eight weeks after implantation (FIG. 11B), although the calcium deposition in both groups increased with the implantation period. The calcium deposition in the PLGA scaffold group with no HA was far less than that in both HA-containing scaffold groups.

The PLGA/HA scaffolds fabricated by the GF/PL method exhibited a higher exposure of HA at the scaffold surface and much better bone formation in vitro and in vivo than those fabricated by the conventional SC/PL method. As compared with other methods for fabricating biodegradable polymer/ceramic composite scaffolds, the GF/PL method has a number of advantages.

First, the GF/PL process avoids the use of organic solvents. Residual organic solvents remaining in scaffolds may damage transplanted cells and surrounding tissues. Furthermore, exposure to organic solvents may inactivate biologically active factors. Therefore, the GF/PL process may cause less denaturation of the growth factors incorporated within the scaffolds.

Second, the GF/PL method can efficiently expose bioceramics at the surface of the polymer/bioceramic composite scaffolds. Staining with a hydrophilic dye and XPS analysis showed that the GF/PL method exposed a significantly higher extent of HA at the scaffold surface than did the conventional SC/PL method in this study (FIG. 6). The SC/PL method causes the polymer coating on the bioceramics by polymer solutions, which hinders the exposure of bioceramics on the scaffold surfaces, while the 5 weeks 8 weeks GF/PL method, which does not use a polymer solution, efficiently exposes the bioceramics on the scaffold surface. Therefore, a GF/PL scaffold can increase the chances of osteogenic cells to make contact with the bioactive ceramics, which enhances osteoblast differentiation and growth.

Third, the GF/PL scaffolds exhibit enhanced mechanical properties as compared to the SC/PL scaffolds. The GF/PL scaffolds had significantly higher compressive and tensile moduli than the SC/PL scaffolds. This might be due to a closer packing of the polymer chains under the high pressure in the GF/PL process and to be tensile alignment of the polymer chains by the polymer elongation that occurs during the foaming. In addition, the residual solvent in the SC/PL scaffolds may function as a plasticizer and make the polymer more ductile. Although the GF/PL composite scaffolds showed greatly enhanced mechanical properties, as compared with the SC/PL composite scaffolds, the measured compressive moduli of the prepared scaffolds is rather low compared to that of human bone. This might be due to the highly porous structure of the fabricated scaffolds and the poor mechanical properties The use of GF/PL scaffolds resulted in enhanced osteogenic potentials in both in vitro and in vivo experiments. Since the SC/PL and GF/PL scaffolds have similar physical properties such as porosity, pore size, and interconnectivity, the difference in osteogenic ability between the two scaffold types might be due to their different surface chemistries. Enhanced bone formation in vitro and in vivo on the GF/PL scaffolds may result from the direct contact of seeded cells with the HA particles exposed on the scaffold surface, which stimulate the cell proliferation and osteogenic differentiation. In contrast, the HA particles would be coated with the polymer, which would hinder interaction with cells in the SC/PL scaffolds. Since the SC/PL scaffold has a large portion of HA particles buried in PLGA polymer, the degradation of PLGA will expose HA particles on its surface. However, the PLGA degradation requires a long time and there will be no acceleration of bone formation by HA during this period.

The ALP activity on the PLGA scaffold without HA did not show any significant changes during the culture period in vitro, but the calcium concentration increased in 56-days in this group. This disparity could be due to the fact that ALP is an early marker for osteogenic differentiation and usually peaks early, while mineralization occurs continuously over the in vitro culture period.

In this study, we used nano-sized HA particles to fabricate PLGA/HA composite scaffolds. Since the highly crystalline HA degrades over long periods of time in vivo, the incompletely degrading residual HA may hinder or slow the complete bone healing. Therefore, to reduce the total amount of HA while enhancing the HA distribution on the scaffold surface, we used nano-sized HA particles, which have a high surface area, to fabricate the composite scaffolds, instead of micro-sized HA particles. Furthermore, the nano-sized HA particles showed improved bioactivity and osteointegration when implanted in the bone defect sites, as compared with the micro-sized HA particles. It has been also reported that protein adsorption and cell adhesion can be enhanced by using nano-sized HA particles instead of micro-sized HA particles.

EXAMPLE 2

Increasing interest has currently been focused on polymer/ceramic composite materials as bone substitutes because these materials have advantages over ceramic scaffolds and polymer scaffolds for bone tissue engineering. Calcium phosphate-based ceramics, such as hydroxyapatite (HA) and tricalcium phosphate, have been used as bone substitutes, but these materials have poor mechanical performance. Most synthetic polymer biomaterials have low surface wettability due to their composition of noncharged elements. Such hydrophobic surfaces are unfavorable to osteogenic cells as they show a lower proliferative and a higher apoptotic rate on hydrophobic surfaces than on hydrophilic surfaces. In addition, these polymeric biomaterials have a bioinert surface that lacks bioactive functions for bone formation, therefore evoking minimal tissue responses. An essential requirement for bone grafts is the ability to create a bond with the living host bone through the formation of a biologically active bonelike apatite layer on the surface of the bone grafts. Bioinert bone substitutes often become encapsulated with fibrous tissues, thereby resulting in disturbed bone formation. Therefore, the addition of calcium phosphate ceramics to biodegradable polymers, such as poly(glycolic acid), poly(L-lactic acid), and poly(D,L-lactic-co-glycolic acid) (PLGA), would allow for better surface wettability as well as enhanced osteoconductivity.

Figure 12A:
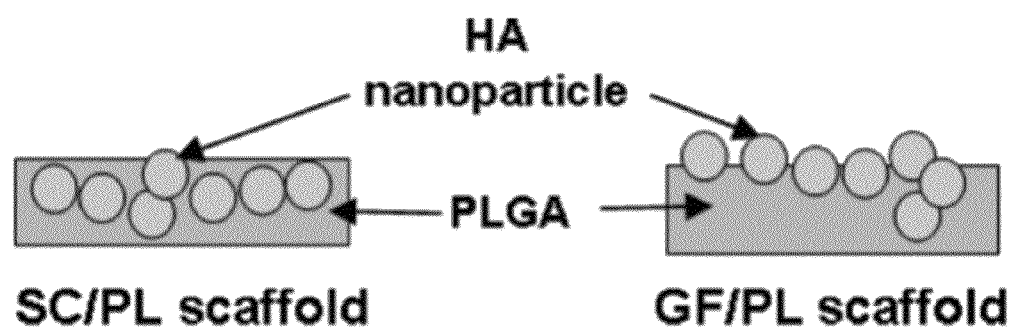
FIG. 12(A) Schematic illustration of the exposure of HA nanoparticles to the surface of scaffolds fabricated by the GF/PL and SC/PL methods.
Figure 12B:
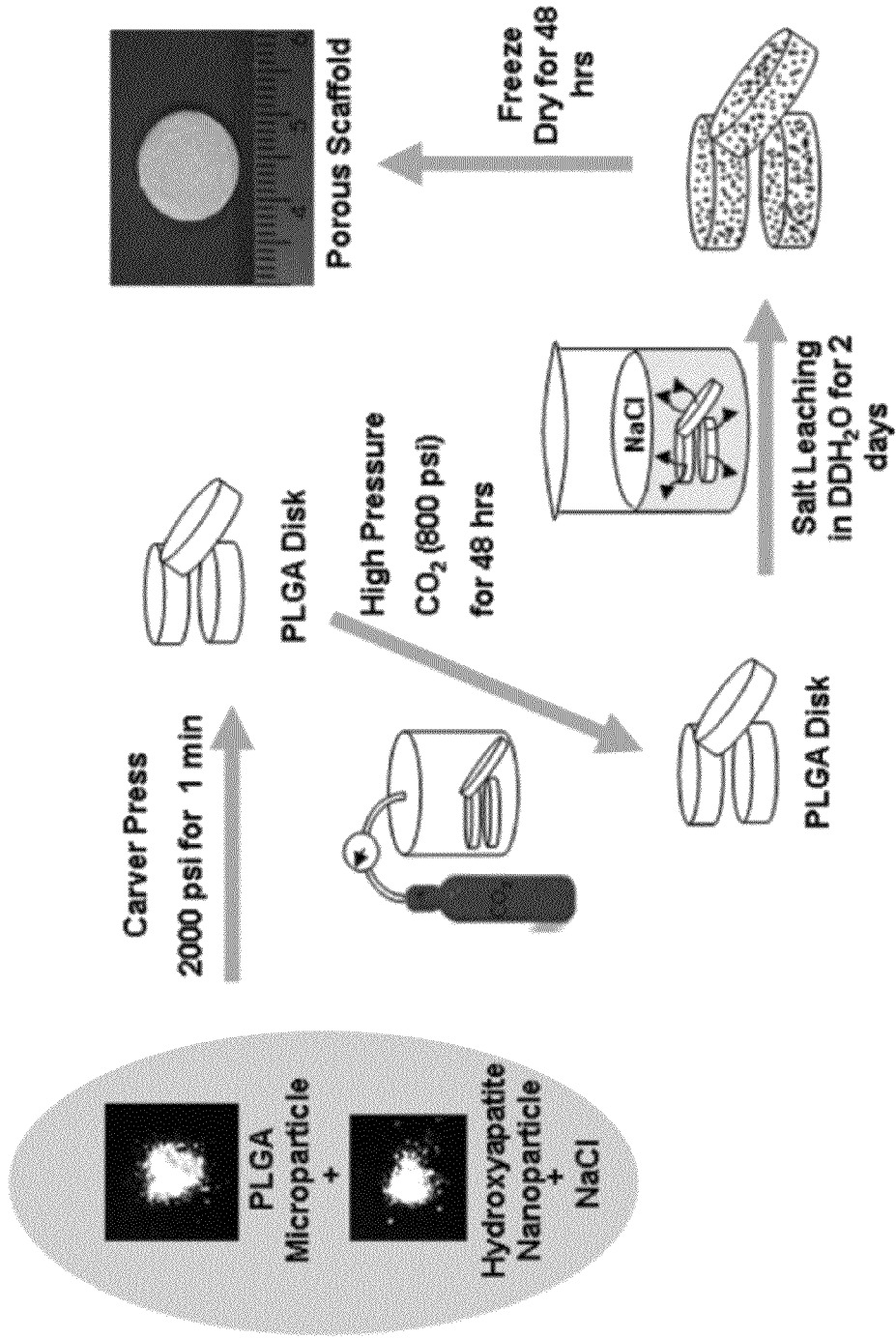
FIG. 12(B) Schematic illustration of the fabrication of PLGA/HA composite scaffolds with the GF/PL method.

Most of the previously available methods for the fabrication of polymer/ceramic composite scaffolds, such as the solvent casting and particulate leaching (SC/PL) method and the phase separation method, use organic solvents. However, residual solvents in the scaffolds may be harmful to transplanted cells or host tissues. Furthermore, polymer coating on the ceramic particles by polymer solutions may hinder the exposure of the ceramics to the scaffold surfaces [FIG. 12(A)], which decreases the chance of contact between the osteogenic cells and the bioactive ceramics. We thought the gas foaming and particulate leaching (GF/PL) method would efficiently expose bioactive ceramics on the scaffold surfaces and that these efficiently exposed ceramics would thus enhance the osteoconductivity and wetability of the scaffolds. In the present study, we tested this hypothesis by transplanting scaffolds to rat skull critical size defects and examining the bone formation. The HA exposure to the scaffold surface was compared between GF/PL scaffolds and SC/PL scaffolds. Bone regeneration using GF/PL scaffolds was evaluated in vivo and compared with that using SC/PL scaffolds.

Figure 10B:
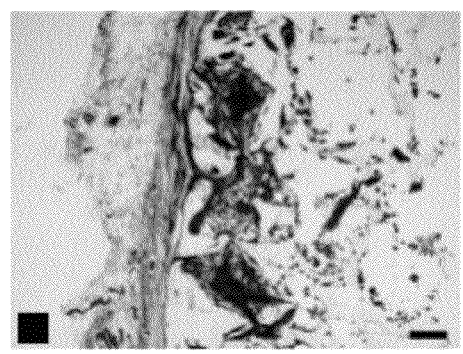
Figure 10C:
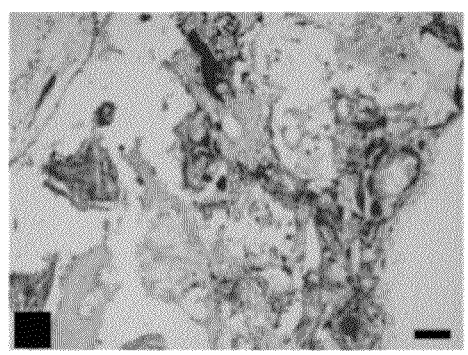
Figure 10D:
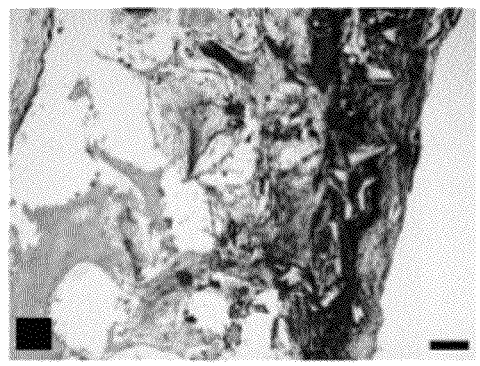
Figure 10E:
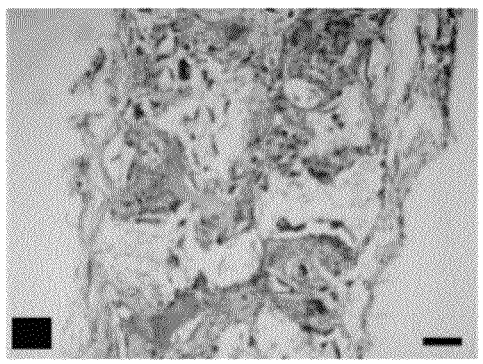
Figure 10F:

Porous PLGA/HA composite scaffolds were fabricated by the modification of a previously described GF/PL method [FIG. 10(B)] of Harris L D, Kim B S, Mooney D J. *Open pore biodegradable matrices formed with gas foaming*, J Biomed Mater Res 1998; 42: 396-402; PLGA/HA composites were prepared with 75:25 PLGA particles (diameter=100-200 mm, molecular weight =100,000 Da; Birmingham Polymers, Birmingham, Ala.), HA nanoparticles (diameter=approximately 100 nm; Berkeley Advanced Biomaterials, Berkeley, Calif.), and sodium chloride particles (diameter=100-200 mm; Sigma, St. Louis, Mo.). The mixed PLGA/HA/NaCl mass ratio was 1:1:9. The mixture was loaded into a disk mold (diameter=13.5 mm; Aldrich Chemical, Milwaukee, Wis.) and compressed at 2000 psi for 1 min using a Carver Laboratory Press (Fred S. Carver, Menominee Falls, Wis.) to yield solid disks with a thickness of 1 mm. The samples were exposed to high pressure $CO_2$ gas (800 psi) for 48 h to saturate the polymer with the gas. Next, a thermodynamic instability was created by decreasing the gas pressure to ambient pressure. The NaCl particles were subsequently removed from the scaffolds by leaching the scaffolds in distilled water for 48 h. PLGA scaffolds without HA were also fabricated by the GF/PL method (GF/PL-no HA).

Porous PLGA/HA scaffolds were also fabricated by the modification of a previously described SC/PL method set forth in Lu H H, El-Amin S F, Scott K D, Laurencin C T, *Three-dimensional, bioactive, biodegradable polymer-bioactive glass composite scaffolds with improved mechanical properties support collagen synthesis and mineralization of human osteoblast-like cells in vitro*, J Biomed Mater Res A 2003; 64: 465-474; Cho S W, Kim I K, Lim S H, Kim D I, Kang S W, Kim S H, et al. *Smooth muscle-like tissues engineered with bone marrow stromal cells*, Biomaterials 2004; 25:2979-86; and Kim B S, Jeong S I, Cho S W, Nikolovski J, Mooney D J, Lee S H, et al., *Tissue engineering of smooth muscle under a mechanically dynamic condition*, J Microbiol Biotech 2003; 13:841-5 and used as another control. In this process, PLGA was dissolved in methylene chloride (J. T. Baker, Phillipsburg, N.J.) at a 10% (w/v) concentration, and HA and NaCl were added to the PLGA solution at the same size and ratio as those of the GF/PL scaffolds. This mixture was loaded into Teflon cylinders (diameter=21.5 mm, height=25 mm; Cole-Parmer Instrument Company, Vernon Hills, Ill.). Following solvent evaporation, polymer disks with entrapped salt particles were removed from the molds. The salt was removed by immersing disks in distilled water for 48 h. The dimension of fabricated SC/PL scaffolds was same with that of GF/PL scaffolds.

The morphologies of the scaffolds were examined using a scanning electron microscope (SEM; JSM-6330F, JEOL, Tokyo, Japan). Samples were dehydrated in ascending grades of ethanol, dried, and mounted on an aluminum stub using a double-sided carbon tape. The specimens were coated with platinum using a Sputter Coater (Cressington 108, Cressington Scientific Instruments, Cranberry, Pa.) and examined with SEM at an acceleration voltage of 10 kV. The porosity of fabricated scaffolds was measured using mercury intrusion porosimetry (Autopore IV 9500, Micromeritics Instrument Corporation, Norcross, Ga.). A contact angle of 1308 for mercury on the scaffold was used for this analysis. Compression and tensile tests were performed with an Instron mechanical tester (Instron 4201, Instron®, Canton, Mass.). The scaffold samples were cut into 1×1 cm$^2$ for compression testing. For tensile testing, the samples (1 ×1 cm$^2$) were attached to cardboard using epoxy glue. The sample was centered in a 7 mm slot in the centre of the card board and then glued to standardize the gauge length. Compression and tensile tests were performed with a constant strain rate of 1 mm/min. The moduli were determined from the slopes in the initial elastic portion of the stress-strain diagram. To examine the distribution and the extent of surface exposure of HA in the scaffolds, HA exposed to the scaffold surface was visualized with a hydrophilic dye (trypan blue) staining or von Kossa's silver staining. For trypan blue (Sigma) staining, the residual dye was removed by sonication in 100% ethanol. For the von Kossa staining, scaffolds were immersed in 2% (w/v) silver nitrate (Sigma) solution and placed directly in front of a bright lamp for 30 min. Scaffolds were then rinsed in distilled water. The surface of the PLGA/HA scaffolds was then examined with a microscope (Camscope, Samtech, Seoul, South Korea). The scaffolds were then tested for their wettability.

For this, trypan blue solution was dropped on top of the scaffold and the time required for complete absorption of the solution into the scaffold was measured.

Sprague-Dawley rats (8-week-old males, n=24; SLC, Tokyo, Japan) were anesthetized with an intraperitoneal injection (5 mg/kg body wt.) of a 4:1 solution of ketamine hydrochloride (Ketara, Yuhan, Seoul, South Korea) and xylazine (Rompun, Bayer Korea, Seoul, South Korea). After shaving the scalp hair, a longitudinal incision was made in the midline of cranium from the nasal bone to the posterior nuchal line, and the periosteum was elevated to expose the surface of the parietal bones. Using a surgical trephine bur (Ace Surgical Supply, Brockton, Mass.) and a low-speed micromotor, a circular and transosseous defect (8 mm in diameter) was produced in the parietal bone. The drilling site was irrigated with saline and the bleeding point was electrocauterized. The defect was filled with the fabricated scaffolds. The periosteum and skin were then closed in layers with resorbable 4-0 Vicryl® (Ethicon, Edinburgh, UK) sutures. The rats were housed singly after surgery and received humane care in compliance with Seoul National University Guidelines for the care and use of laboratory animals. The implants were retrieved 8 weeks after implantation for analyses.

Following euthanasia, the craniums including implanted scaffolds were retrieved at 8 weeks after surgery. Samples were fixed immediately in a 10% (v/v) neutral buffered formalin solution. One specimen from each condition was scanned using a desktop X-ray 3D micro computed tomography (CT; Skyscan 1072®, SkyScan bvba, Aartselaar, Belgium) to analyze bone formation. A microfocus X-ray tube with a focal spot of 8 mm was used as a source and a 1024 ×1024 12-bit digital CCD X-ray detector were used. The coronal view was imaged at 8 mm slices. Each coronal CT image was reconstructed by V-works™(CyberMed, Seoul, South Korea) to visualize the three-dimensional volume image of new bone and to examine the microarchitecture of the regenerated bone tissue.

After collection of the micro CT scans, all samples (n=24) were decalcified in EDTA (pH 6.0) for 7 days and embedded in paraffin. The tissue blocks were sectioned at a 4 mm thickness and stained with hematoxylin and eosin (H & E) and Masson's trichrome. The Masson's trichrome-stained midportion sections were examined with a microscope for histomorphometry. The percentage of bone-occupying space within the constructs was measured using an image analysis system (KS400, Zeiss, Munich, Germany) coupled to a light microscope. The bone formation area was expressed as percent bone area in available pore space (bone area/pore area=100%).

Quantitative data were expressed as the mean 6 standard deviation. Statistical comparisons were carried out using analysis of variance (ANOVA, SAS Institute, Cary, N.C.). A value of p<0.05 was considered to be statistically significant.

Figure 13A:
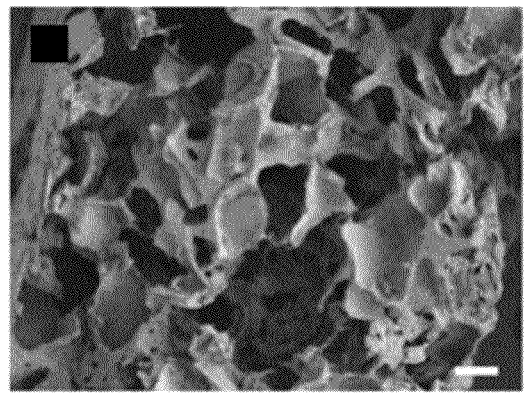
FIGS. 13(A)-(B). Scanning electron micrographs of the PLGA/HA composite scaffolds fabricated with (A) the SC/PL method and (B) the GF/PL method.
Figure 13B:
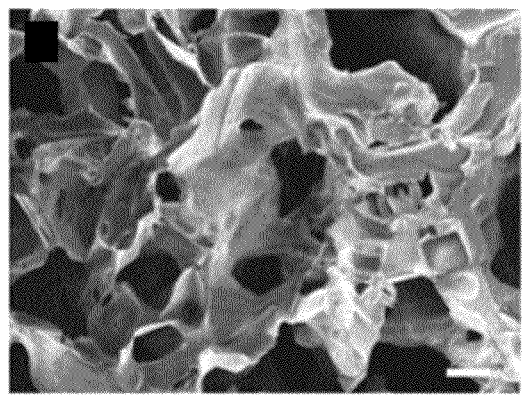

Gas foaming and subsequent salt leaching of scaffolds containing a high percentage of NaCl particles led to the formation of highly porous structures with no evidence of an external, non porous skin layer [FIG. 13(B)]. The GF/PL scaffolds exhibited highly porous and open-pore structures. The pore structure observed in the cross-sections of the GF/PL scaffolds was similar to that of the SC/PL scaffolds [FIG. 13(A)]. The average porosities of the GF/PL and SC/PL scaffolds were (91±3)% and (86±3)%, respectively.

Figure 14A:
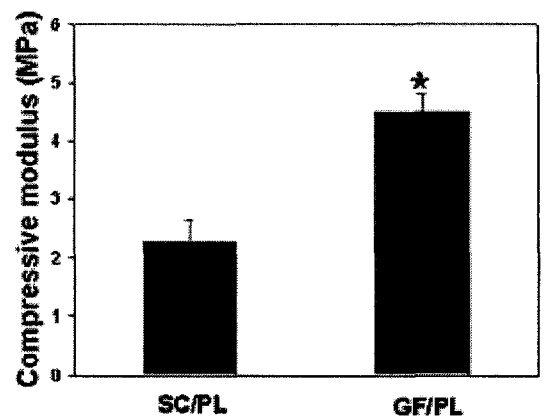
FIGS. 14(A)-(C) The compressive modulus (A) and tensile modulus (C) of the SC/PL and GF/PL scaffolds. (B) Typical tensile stress strain curve of the SC/PL and GF/PL scaffolds.
Figure 14B:
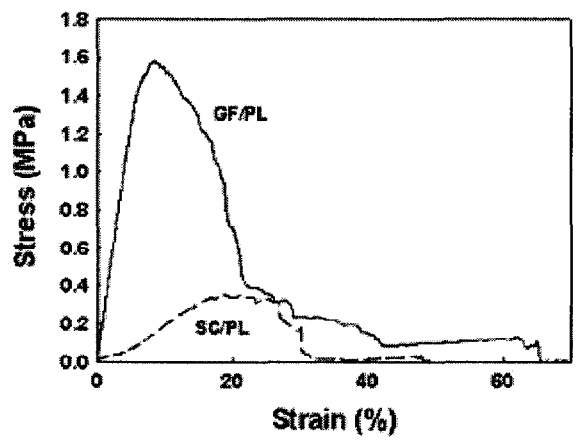
Figure 14C:
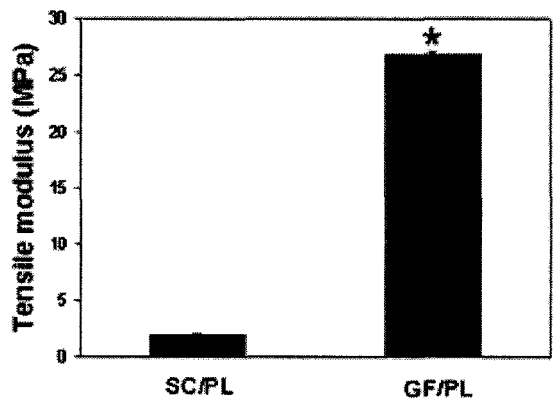

The mechanical properties of the scaffolds were assessed using compressive and tensile mechanical tests. The GF/PL scaffolds exhibited enhanced mechanical properties as compared to the SC/PL scaffolds. The average compression modulus was 2.3±0.4 and 4.5±0.3 MPa (p<0.05) for the SC/PL and GF/PL scaffolds, F3 respectively [FIG. 14(A)]. The average tensile modulus was 2.0 6 0.1 and 26.9 6 0.2 MPa (p<0.05) for the SC/PL and GF/PL scaffolds, respectively [FIG. 14(B,C)]. These data represent a 99% increase in compression modulus and a 1331% increase in tensile modulus.

Figure 15A:
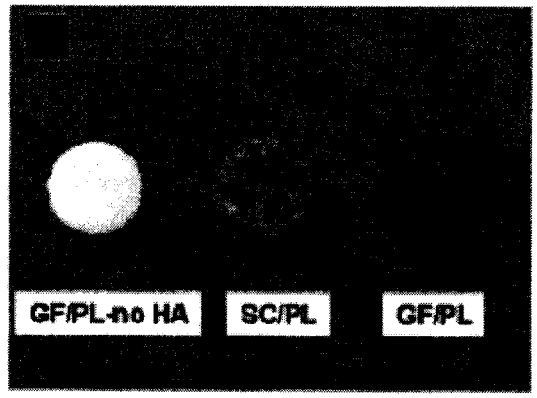
FIGS. 15(A)-(E) Macroscopic images of the three types of scaffolds
Figure 15B:
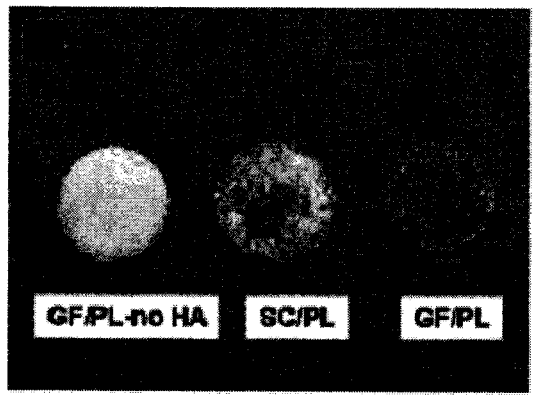
Figure 15C:
Figure 15D:
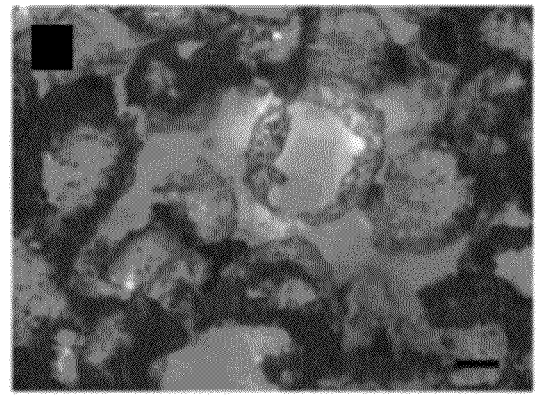
Figure 15E:
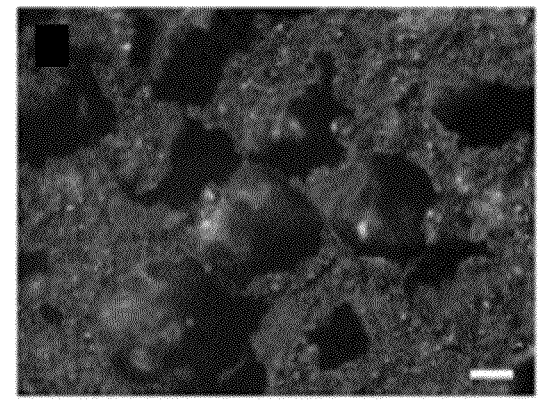

To determine whether the scaffold fabrication process affected the extent of HA exposure to the scaffold surface, the exposed HA was stained with von Kossa's silver nitrate [FIG. 15(A)] and a hydrophilic trypan blue dye [FIG. 4(B)]. HA was stained more abundantly in the GF/PL scaffolds than in the SC/PL scaffolds with both staining methods (FIG. 15). In contrast, GF/PL scaffolds without HA (GF/PL-no HA scaffolds) showed no positive staining with either staining method [FIG. 15(A-C)].

Figure 16A:
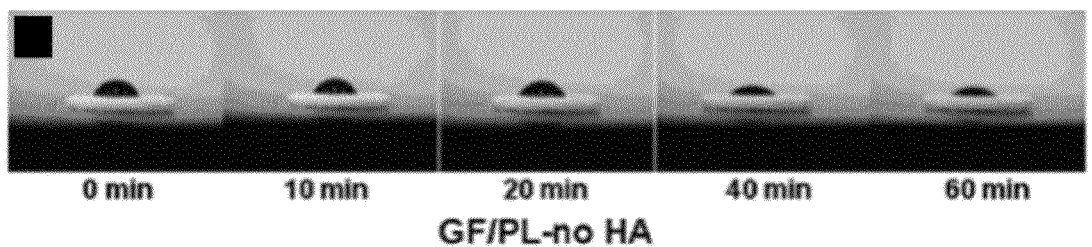
FIGS. 16(A)-(C) Photographs showing wettability of the three types of scaffolds.
Figure 16B:
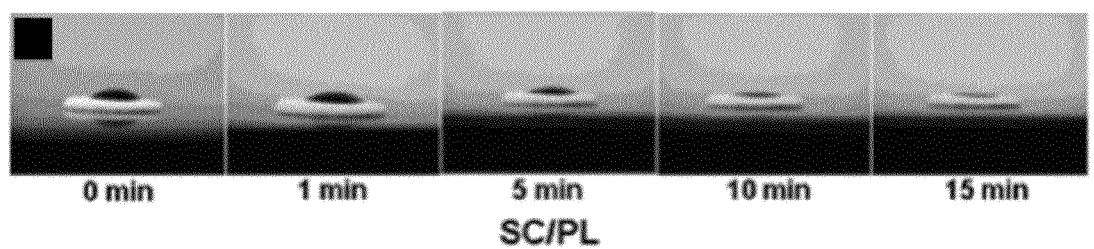
Figure 16C:
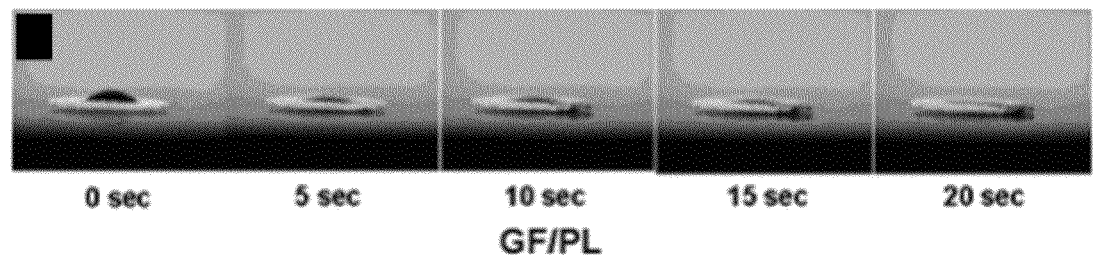
Figure 17A:
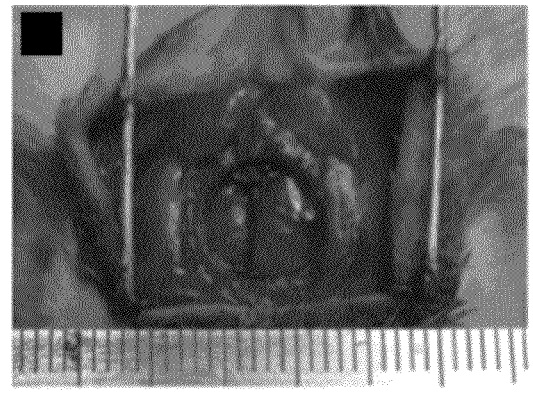
FIG. 17 (A) Photograph showing defect created in rat cranium.
FIG. 17(B) Photograph showing the implanted scaffold
FIG. 17(D) Gross view of the cranium containing the GF/PL no HA scaffold
Figure 17B:
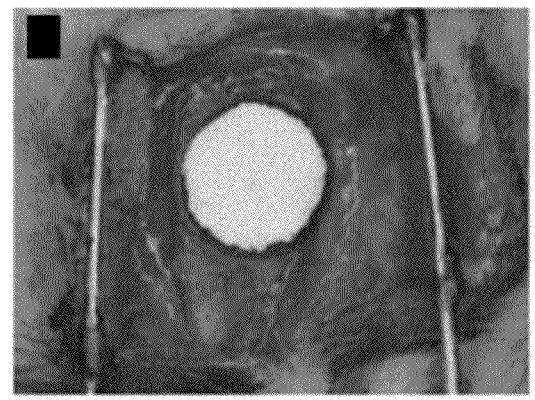
Figure 17C:
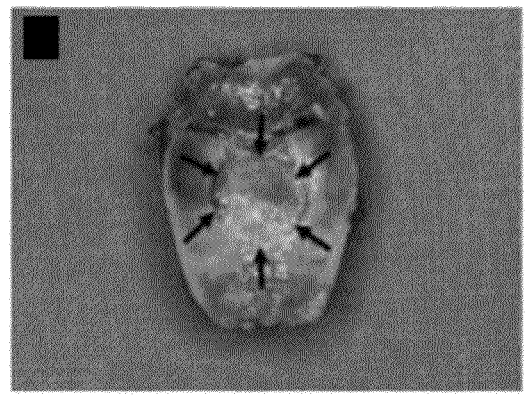
Figure 17D:
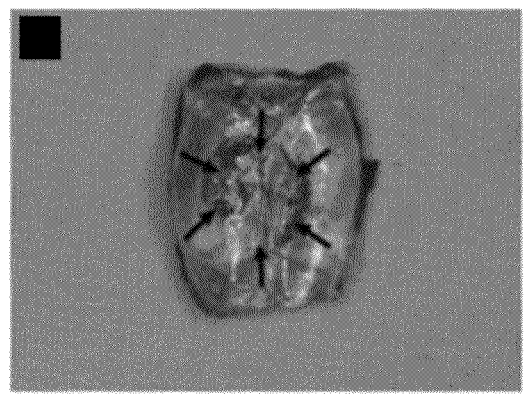

To evaluate whether the hydrophilicity of the PLGA scaffold and PLGA/HA composite scaffolds could be improved by the addition of HA and by the application of different fabrication processes, respectively, the wettability of GF/PL, SC/PL, and GF/PL-no HA scaffolds was measured. When a trypan blue dye solution was dropped to the scaffolds, the solution was completely absorbed into the GF/PL scaffold within 5 s [FIG. 16(C)]. However, it was not absorbed at all into F5 the GF/PL-no HA scaffold even after 60 min because of the hydrophobic character of the scaffold [FIG. 16(A)]. The SC/PL scaffolds absorbed the dye solution slowly within 15 min [FIG. 16(B)]. The faster wetting of the GF/PL scaffold compared to that of the SC/PL scaffold correlated with the amount of HA exposed onto the scaffold surface.

Figure 18A:
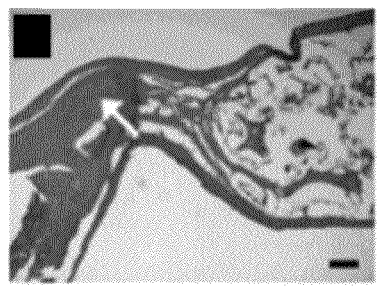
FIGS. 18(A)-(F) Histological evaluations of specimens retrieved at 8 weeks after implantation showing Hematoxylinandeosin (H&E) staining (A,D) GF/PL-no HA scaffold, (B,E) SC/PL scaffold, and (C,F) GF/PL scaffold at 8 weeks. (A, B, and C) Defect edge and (D, E, and F) midsection of the scaffolds.
Figure 18B:
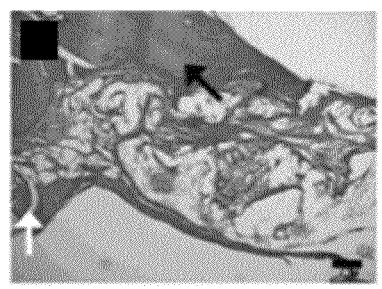
Figure 18C:
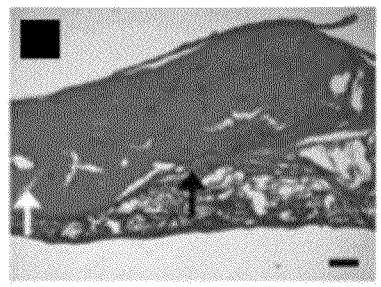
Figure 18D:
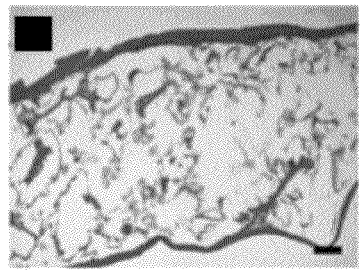
Figure 18E:
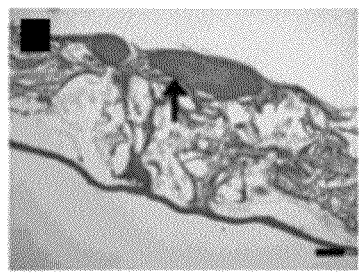
Figure 18F:
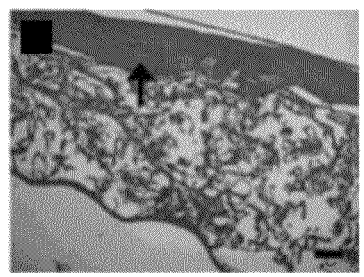
Figure 19A:
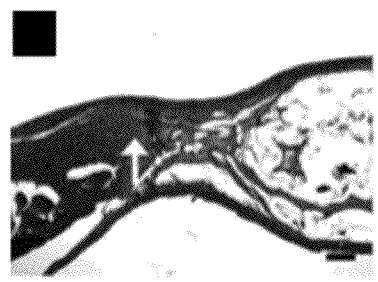
FIGS. 19(A)-(F) Histological evaluations of specimens retrieved at 8 weeks after implantation. Masson's trichrome staining. (A,D) GF/PL-no HA scaffold, (B,E) SC/PL scaffold, and (C,F) GF/PL scaffold at 8 weeks. (A,B, and C) Defect edge and (D, E, and F) mid-section of the scaffolds (blank arrow, original bone; solid arrow, new bone).]
Figure 19B:
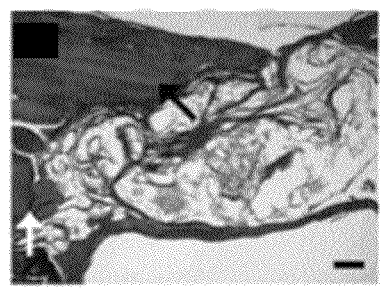
Figure 19C:
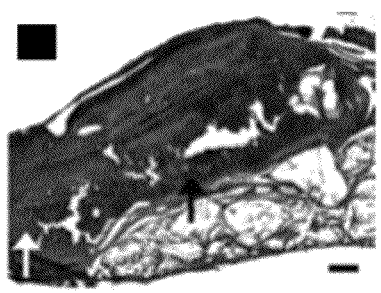
Figure 19D:
Figure 19E:
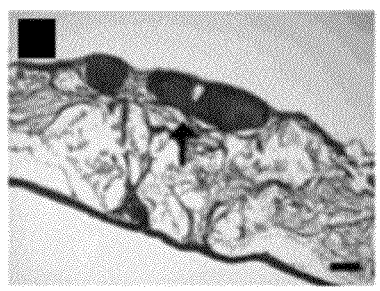
Figure 19F:
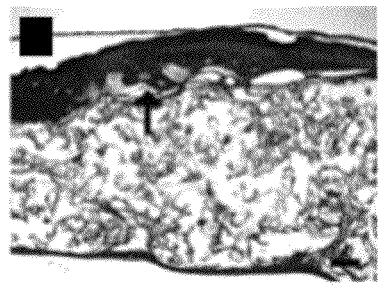
Figure 20:
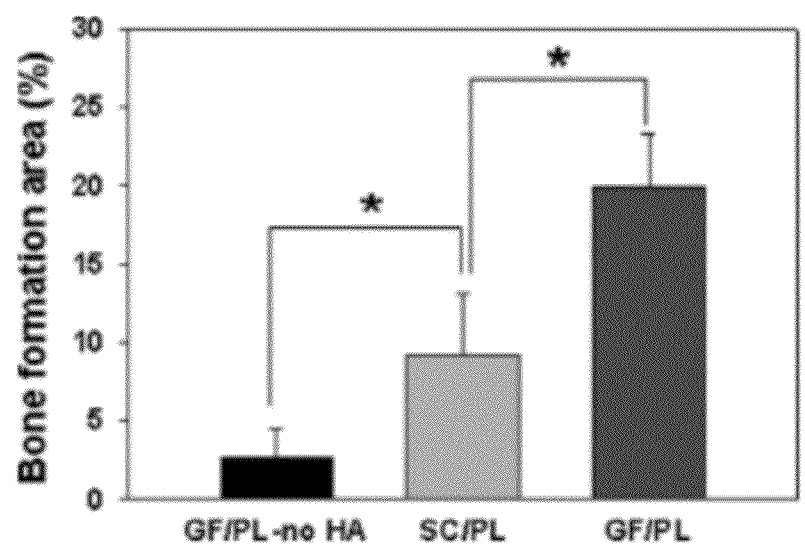
FIG. 20 Graph showing higher bone formation in GF/PL scaffolds compared to SC/PL and GF/PL no HA scaffolds.

The implantation of both types of the PLGA/HA composite scaffolds into critical size defects in rat skulls resulted in enhanced bone formation in vivo compared with the PLGA scaffold (FIG. 17). Eight weeks after implantation, new bone with lamellar structures and osteoid formation was appreciated in the SC/PL [FIGS. 18(B,E) and FIGS. 19(B,E)] and GF/PL [FIGS. 18(C,F) and 19(C,F)]scaffolds at F8 the defect edges and midsites of the grafts. The bone formation area in the GF/PL scaffold was higher than that in the SC/PL scaffold and GF/PL-no HA scaffold at 8 weeks after implantation (FIG. 20). The PLGA polymer with no HA produced very little new bone in vivo in the 8 weeks following implantation [FIGS. 18(A,D) and 19(A,D)]. Most of the pores of the PLGA scaffolds were filled with loose fibrous connective tissues without evidence of bone formation [FIGS. 18(D) and 19(D)]. Over time, the PLGA seemed to continuously degrade without adverse reactions, and had not completely resorbed during the 8 weeks following implantation.

Figure 21A:
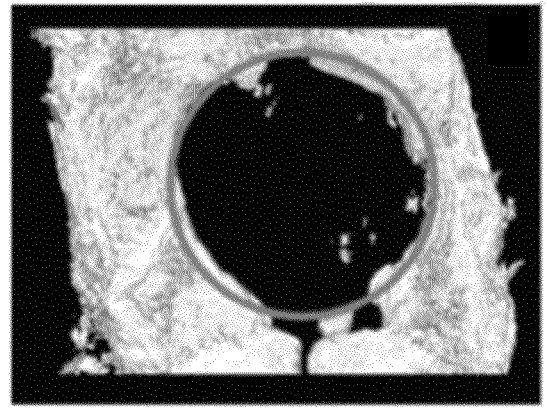
FIGS. 21(A)-(C) Images of micro CT analysis of specimens retrieved 8 weeks after implantation. A-GF/PL no HA; B SC/PL and C GF/PL scaffold.
Figure 21B:
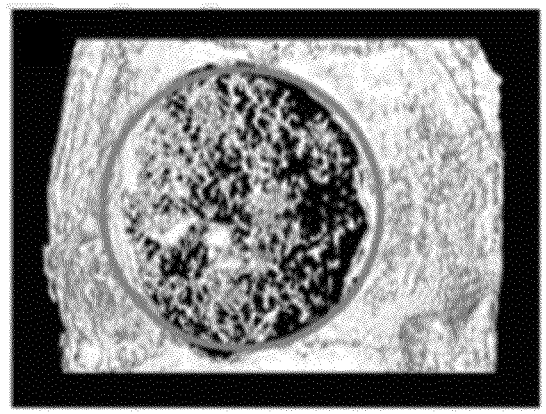
Figure 21C:
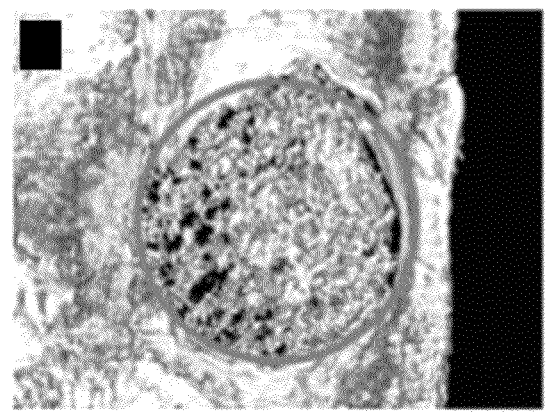

Micro CT evaluation allowed the mineralized tissues to distinguish from the remaining soft tissues present inside the defects (FIG. 21). The reconstructed three-dimensional images showed the formation of new bone inside both types of the PLGA/HA composite scaffolds. Within the scaffolds, dispersed irregular-shaped mineralized tissues were found throughout the implant. Mineralized tissue areas were significantly larger in the GF/PL scaffolds than in the SC/PL and GF/PL-no HA scaffolds.

As compared to the conventional methods for the fabrication of biodegradable polymer/ceramic composite scaffolds, the GF/PL method has several advantages. First, the GF/PL method avoids the use of organic solvents. Residual organic solvents remaining in the scaffold may damage transplanted cells and surrounding tissues. Furthermore, exposure to organic solvents may inactivate biologically active factors. Therefore, the GF/PL method may cause less denaturation of growth factors incorporated within the scaffold. Second, the GF/PL scaffold exhibits a higher exposure of HA to the scaffold surface than the SC/PL scaffold. The SC/PL method causes the coating of the HA by the polymer solution, which hinders the exposure of HA to the scaffold surfaces, while the GF/PL method efficiently exposes HA to the scaffold surface due to the lack of a requirement of a polymer solution. Therefore, the GF/PL scaffold can increase the chances of contact between the osteogenic cells and the bioactive ceramics that are exposed on the scaffold surface.

In addition, the enhanced exposure of hydrophilic HA nanoparticles to the scaffold surface affected the hydrophilicity of the scaffold. The hydrophobic surfaces of most synthetic polymer biomaterials are unfavorable to osteogenic cells, because they show a lower proliferative rate and a higher apoptotic rate on hydrophobic surface than on hydrophilic surfaces There fore the addition of HA to the PLGA scaffold may enhance the scaffolds hydrophilicity as well as its osteoconductivity. The scaffold fabrication process also affected the hydrophilicity of the PLGA/HA scaffolds. The faster wetting of the GF/PL scaffold compared with the SC/PL scaffold was likely due to higher amount of HA exposed to the surface of the GF/PL scaffold.

The GF/PL scaffold exhibited enhanced bone regeneration in vivo when compared to the SC/PL scaffold. The PLGA in the PLGA/HA scaffolds is bioinert for bone formation. However, the HA exposed to the scaffold surface stimulates bone formation. Enhanced bone formation on the GF/PL scaffolds may result from the direct contact of migrating osteogenic cells from the surrounding tissues with the HA particles exposed to the scaffold surface, which then stimulates cell proliferation and osteogenic differentiation. In contrast, the SC/PL scaffold had HA particles coated with the polymer, which hindered interaction of HA with the osteogenic cells and thus hindered the bone formation process.

In this study, we used nanosized HA particles to fabricate PLGA/HA composite scaffolds. Since the highly crystalline HA degrades over a long period in vivo, incompletely degraded residual HA may hinder or slow the complete bone healing. Therefore, to reduce the total amount of HA while enhancing the HA exposure to the scaffold surface, nanosized HA particles, which have a high surface area, were used to fabricate the composite scaffolds instead of microsized HA particles. Furthermore, nanosized HA particles showed improved bioactivity and osteointegration when implanted to the bone defect site compared to the microsized HA particles. Protein adsorption and cell adhesion have also been reported to be enhanced by the use of nanosized HA particles compared to microsized HA particles.

The PLGA/HA composite scaffolds of the present invention show enhanced hydrophilicity and osteoconductivity compared with the SC/PL scaffolds. This enhancement was most likely due to a higher extent of exposure of HA particles to the scaffold surface. The biodegradable polymer/bioceramic composite scaffolds fabricated by the GF/PL method could enhance bone regeneration efficacy for the treatment of bone defects compared with conventional composite scaffolds.

One of skill in the art will be readily aware that while polyglycolic acid polymers are most preferred due to their osteoconductive and osteoinductive properties, other polymers can be used to achieve similar results to the present invention. Such other polymers include but are not limited to a bioabsorbable, or biodegradable, synthetic polymer such as a polyanhydride, polyorthoester, polylactic acid, and copolymers or blends thereof. Non-degradable materials can also be used to form the matrix. Examples of suitable materials include ethylene vinyl acetate, derivatives of polyvinyl alcohol, teflon, and nylon. The preferred non-degradable materials are a polyvinyl alcohol sponge, or alkylation, and acylation derivatives thereof, including esters. Collagen can be used, but is not as controllable and is not preferred. These materials are all commercially available. Non-biodegradable polymer materials can be used, depending on the ultimate disposition of the growing cells, including polymethacrylate and silicon polymers.

Those of skill in the art are familiar with the use of bone graft materials. The present invention can be used in the same manner as any other bone graft material. In a preferred delivery system, the bone graft material is mixed with polyethylene glycol to form a paste. The material can be premixed and sold in a syringe for easy application or can be mixed at the point of use and delivered via any convenient means. When provided in a dry state, any suitable biocompatible fluid can be used to wet the material and create a paste for administration to the patient. Examples of such biocompatible fluid wetting agents include, but are not limited to: dextrose, glucose, maltose or sodium chloride solutions, blood, serum, platelet concentrate, bone marrow aspirate, and synovial fluid. A biological fluid can be used in the form obtained from the biological source, or it can be processed by application of one or more desired useful techniques, examples of which include, separation techniques, such as filtration (macro-, micro-, or ultra-filtration); purification techniques, such as dialysis; concentration techniques; and sterilization techniques.

One of skill in the art will recognize that other biological components including but not limited to proteins, growth factors, cells, stem cells, osteoblasts or such other components that will promote bone growth or maturation of the bone graft.

The description of the teachings is merely exemplary in nature and, thus, variations that do not depart from the gist of the teachings are intended to be within the scope of the teachings. Such variations are not to be regarded as a departure from the spirit and scope of the teachings.

References 1. de Boer H H. The history of bone grafts. Clin Orthop Relat Res 1988; 226:292-8.
2. Vacanti C A, Kim W, Upton J, Vacanti M P, Mooney D, Schloo B, et al. Tissue-engineered growth of bone and cartilage. Transplant Proc 1993; 25:1019-21.
3. Bonfiglio M, Jeter W S. Immunological responses to bone. Clin Orthop Relat Res 1972; 87:19-27.
4. Coombes A G, Meikle M C. Resorbable synthetic polymers as replacements for bone graft. Clin Mater 1994; 17:35-67.
5. Rizzi S C, Heath D J, Coombes A G, Bock N, Textor M, Downes S. Biodegradable polymer/hydroxyapatite composites: surface analysis and initial attachment of human osteoblasts. J Biomed Mater Res 2001; 55:475-86.
6. Laurencin C T, Attawia M, Borden M D. Advancements in tissue engineered bone substitutes. Curr Opin Orthop 1999; 10:445-51.
7. Ambrosio A M, Sahota J S, Khan Y, Laurencin C T. A novel amorphous calcium phosphate polymer ceramic for bone repair: I. Synthesis and characterization. J Biomed Mater Res 2001; 58: 295-301.
8. Marra K G, Szem J W, Kumta P N, DiMilla P A, Weiss L E. In vitro analysis of biodegradable polymer blend/hydroxyapatite composites for bone tissue engineering. J Biomed Mater Res 1999; 47:324-35.
9. Wang M. Developing bioactive composite materials for tissue replacement. Biomaterials 2003; 24:2133-51.
10. Van Landuyt P, Li F, Keustermans J P, Streydio J M, Delannay F, Munting E. The influence of high sintering temperatures on the mechanical properties of hydroxyapatite. J Mater Sci Mater Med 1995; 6:8-13.
11. Khan Y M, Katti D S, Laurencin C T. Novel polymer-synthesized ceramic composite-based system for bone repair: An in vitro evaluation. J Biomed Mater Res A 2004; 69:728-37.
12. Kikuchi M, Cho S-B, Suetsugu Y, Tanaka J. In vitro tests and in vivo tests developed TCP/CPLA composites. Bioceramics 1997; 10: 407-10.
13. Reis R L, Cunha A M, Fernandes M H, Correia R N. Bioinert and biodegradable polymeric matrix composites filled with bioactive SiO2-3CaO♦P2O5-MgO glasses and glass-ceramics. Bioceramics 1997; 10:415-8.
14. Piattelli A, Franco M, Ferronato G, Santello M T, Martinetti R, Scarano A. Resorption of composite polymer-hydroxyapatite membranes: a time-course study in rabbit. Biomaterials 1997; 18: 629-33.
15. Lu L, Currier B L, Yaszemski M J. Synthetic bone substitutes. Curr Opin Orthop 2000; 11:383-90.
16. Peter S J, Lu L, Kim D J, Mikos A G. Marrow stromal osteoblast function on a poly(propylene fumarate)/beta-tricalcium phosphate biodegradable orthopaedic composite. Biomaterials 2000; 21:1207-13.
17. Wei G, Ma P X. Structure and properties of nano-hydroxyapatite/polymer composite scaffolds for bone tissue engineering. Biomaterials 2004; 25:4749-57.
18. Guan L, Davies J E. Preparation and characterization of a highly macroporous biodegradable composite tissue engineering scaffold. J Biomed Mater Res A 2004; 71:480-7.
19. Zhang R, Ma P X. Poly(alpha-hydroxyl acids)/hydroxyapatite porous composites for bone-tissue engineering. I. Preparation and morphology. J Biomed Mater Res 1999; 44:446-55.
20. Lee S H, Kim B S, Kim S H, Kang S W, Kim Y H. Thermally produced biodegradable scaffolds for cartilage tissue engineering. Macromol Biosci 2004; 4:802-10.
21. Yang S, Leong K F, Du Z, Chua C K. The design of scaffolds for use in tissue engineering. Part I. Traditional factors. Tissue Eng 2001; 7:679-89.
22. Jung Y, Kim S S, Kim Y H, Kim S H, Kim B S, Kim S, et al. A poly(lactic acid)/calcium metaphosphate composite for bone tissue engineering. Biomaterials 2005; 26:6314-22.
23. Jung Y, Kim S H, Kim S S, You H J, Kim B S, Kim S, et al. Tissue engineered bone formation with polymer/ceramic composites by press-and-baking method. Key Eng Mater 2005; 288:79-82.
24. Harris L D, Kim B S, Mooney D J. Open pore biodegradable matrices formed with gas foaming. J Biomed Mater Res 1998; 42: 396-402.
25. Cho S W, Kim I K, Lim S H, Kim D I, Kang S W, Kim S H, et al. Smooth muscle-like tissues engineered with bone marrow stromal cells. Biomaterials 2004; 25:2979-86.
26. Cho S W, Kim S S, Rhie J W, Cho H M, Choi C Y, Kim B S. Engineering of volume-stable adipose tissues. Biomaterials 2005; 26: 3577-85.
27. Kim B S, Jeong S I, Cho S W, Nikolovski J, Mooney D J, Lee S H, et al. Tissue engineering of smooth muscle under a mechanically dynamic condition. J Microbiol Biotech 2003; 13:841-5.
28. Whitson S W, Whitson M A, Bowers Jr. D E, Falk M C. Factors influencing synthesis and mineralization of bone matrix from fetal bovine bone cells grown in vitro. J Bone Miner Res 1992; 7:727-41.
29. Ekholm M, Hietanen J, Tulamo R M, Muhonen J, Lindqvist C, Kellomaki M, et al. Tissue reactions of subcutaneously implanted mixture of epsilon-caprolactone-lactide copolymer and tricalcium phosphate. An electron microscopic evaluation in sheep. J Mater Sci Mater Med 2003; 14:913-8.
30. Jaiswal N, Haynesworth S E, Caplan A I, Bruder S P. Osteogenic differentiation of purified, culture-expanded human mesenchymal stem cells in vitro. J Cell Biochem 1997; 64:295-312.
31. Lewandrowski K U, Bondre S P, Wise D L, Trantolo D J. Enhanced bioactivity of a poly(propylene fumarate) bone graft substitute by augmentation with nano-hydroxyapatite. Biomed Mater Eng 2003; 13:115-24.
32. Ginebra M P, Driessens F C, Planell J A. Effect of the particle size on the micro and nanostructural features of a calcium phosphate cement: a kinetic analysis. Biomaterials 2004; 25: 3453-62.
33. Burg K J L, Porter S, Kellam J F. Biomaterial developments for bone tissue engineering. Biomaterials 2000; 21:2347-2359.
34. Akoa M, Aoki H, Kato K. Mechanical properties of sintered hydroxyapatite for prosthetic applications. J Mater Sci 1981; 16:809-812.
35. Anselme K. Osteoblast adhesion on biomaterials. Biomaterials 2000; 21:667-681.
36. Howe A K, Aplin A E, Juliano R L. Anchorage-dependent ERK signaling-mechanisms and consequences. Curr Opin Genet Dev 2002; 12:30-35.

37. Bigi A, Boanini E, Panzavolta S, Roveri N, Rubini K. Bone like apatite growth on hydroxyapatite-gelatin sponges from simulated body fluid. J Biomed Mater Res 2002; 59:709-715.
38. Stupp S I, Ciegler G W. Organoapatites: Materials for artificial bone. I. Synthesis and microstructure. J Biomed Mater Res 1992; 26:169-183.
39. Vandiver J, Dean D, Patel N, Bonfield W, Ortiz C. Nanoscale variation in surface charge of synthetic hydroxyapatite detected by chemically and spatially specific high-resolution force spectroscopy. Biomaterials 2005; 26:271-283.
40. Lu H H, El-Amin S F, Scott K D, Laurencin C T. Three-dimen-sional, bioactive, biodegradable, polymer-bioactive glass composite scaffolds with improved mechanical properties support collagen synthesis and mineralization of human osteoblast-like cells in vitro. J Biomed Mater Res A 2003; 64: 465-474.
41. Li H, Chang J. Preparation and characterization of bioactive and biodegradable wollastonite/poly(D,L-lactic acid) composite scaffolds. J Mater Sci Mater Med 2004; 15:1089-1095.

What is claimed is:

1. A method of fabricating a bone graft material, comprising the steps of:
   selecting biocompatible polymer and salt particles from about 100-200 μm in diameter,
   selecting hydroxyapatite particles less than 1 μm in diameter,
   mixing the biocompatible polymer and hydroxy apatite and NaCl particles, wherein the ratio of biocompatible polymer to hydroxyapatite is from about 1:2 to about 2:1;
   loading the mixture of particles into a mold,
   compressing the mixture with a very high pressure from 1000 to 4000 psi;
   exposing the newly formed composite scaffold to high pressure gas from 400 to 1600 psi and decreasing the gas pressure on the composite scaffold until the pressure returns to ambient pressure, wherein the bone graft material has pores created by the formation of gas bubbles,
   soaking the composite scaffold in an aqueous solution to dissolve and leach out the NaCl particles,
   rinsing and drying the new composite biomaterial; and
   coating the new composite material with apatatite.

2. The method of claim 1 wherein the ratio of biocompatible polymer to hydroxyapatite is about 1:1.

3. The method of claim 1 wherein the ratio of biocompatible polymer to NaCl ranges from 1:4 to 1:18.

4. The method of claim 1 wherein the ratio of biocompatible polymer to NaCl is about 1:9.

5. The method of claim 1 wherein the biocompatible polymer is selected from at least one of the following: poly glycolic acid, poly lactic acid, poly lactic co glycolic acid.

6. The method of claim 5, wherein the biocompatible polymer is poly lactic co glycolic acid.

7. The method of claim 1 wherein the compression pressure is 2000 psi.

8. The method of claim 1 wherein the high pressure gas is at a pressure of 800 psi.

9. The method of claim 1 wherein the method further comprises soaking the biomaterial in a simulated body fluid (SBF) solution comprising NaCl, NaHCO3, Na2SO4, KCl, K2HPO4, MgCl2.6H2O, and CaCl2.2H2O in water to form an apatite layer.

10. A method of claim 1, wherein the coating step is formed uniformly on the surface of the biomaterial.

* * * * *